United States Patent
Fiddes et al.

(10) Patent No.: US 6,294,359 B1
(45) Date of Patent: Sep. 25, 2001

(54) HUMAN BASIC FIBROBLAST GROWTH FACTOR ANALOG

(75) Inventors: John C. Fiddes, Palo Alto; Judith A. Abraham, Sunnyvale; Andrew Protter, Palo Alto, all of CA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/098,628

(22) Filed: Jun. 16, 1998

Related U.S. Application Data

(60) Division of application No. 07/459,739, filed on Feb. 12, 1990, now Pat. No. 5,859,208, which is a continuation-in-part of application No. 07/070,797, filed on Jul. 7, 1987, now abandoned, which is a continuation-in-part of application No. 07/050,706, filed on May 15, 1987, now abandoned, which is a continuation-in-part of application No. 06/869,382, filed on May 30, 1986, now abandoned, which is a continuation-in-part of application No. 06/809,163, filed on Dec. 16, 1985, now Pat. No. 5,439,818, which is a continuation-in-part of application No. 06/775,521, filed on Sep. 12, 1985, now abandoned.

(51) Int. Cl.$^7$ .......................... C12N 15/18; C12N 15/63; C12N 1/21; C12N 5/16; C07K 14/50
(52) U.S. Cl. ................. 435/69.4; 435/243; 435/320.1; 435/325; 530/399
(58) Field of Search ................. 435/69.4, 320.1, 435/325, 243; 530/399

(56) References Cited

U.S. PATENT DOCUMENTS

| | | |
|---|---|---|
| 4,296,100 | 10/1981 | Franco . |
| 4,378,347 | 3/1983 | Franco . |
| 4,399,216 | 8/1983 | Axel et al. . |
| 4,444,760 | 4/1984 | Thomas, Jr. . |
| 5,852,177 | * 12/1998 | Senoo et al. . |

OTHER PUBLICATIONS

Abraham et al., "Human basic fibroblast growth factor: nucleotide sequence and genomic organization" *EMBO J* (1986)5:2523–2528.
Abraham et al., "Nucleotide sequence of a bovine clone encoding the angiogenic protein, basic fibroblast growth factor" *Science* (1986) 233:545–548.
Adelman et al., "In vitro deletional mutagenesis for bacterial production of the 20,000–Dalton form of human pituitary growth hormone" *DNA* (1983) 2:183–193.
Amann et al., "ATG vectors' for regulated high–level expression of cloned genes in *Escherichia coli*" *Gene* (1985) 40:183–190.
Baird et al., "Fibroblast growth factors are present in the extracellular matrix produced by endothelial cells In Vitro: Implications for a role of heparinase–like enzymes in the neovascular response" *Biochem Biophys Res Comm* (1987) 142:428–435.

Baird et al., "Molecular characterization of fibroblast growth factor: Distribution and biological activities in various tissues" *Rec Prog Horm Res* (1986) 42:143–205.
Baird et al., "Radioimmunoassay for fibroblast growth factor (FGF): release by the bovine anterior pituitary in vitro" *Regulatory Peptides* (1985) 10:309–317.
Beaucage et al., "Deoxynucleoside phosphoramidites—a new class of key intermediates for deoxypolynucleotide synthesis" *Tet Letts* (1981) 22:1859–1862.
Beggs, J.D., "Transformation of yeast by a replicating hybrid plasmid" *Nature* (1978) 275:104–109.
Birnboim et al., "A rapid alkaline extraction procedure for screening recombinant plasmid DNA" *Nucleic Acids Res* (1979) 7:1513–1523.
Böhlen et al., "Acidic fibroblast growth factor (FGF) from bovine brain: amino–terminal sequence and comparison with basic FGF" *EMBO J* (1985) 4:1951–1956.
Böhlen et al., "Isolation and partial molecular characterization of pituitary fibroblast growth factor" *Proc Natl Acad Sci USA* (1984) 81:5364–5368.
Bolivar et al., "Construction and characterization of new cloning vehicles. II. A multipurpose cloning system" *Gene* (1977) 2:95–113.
Broach, J.R., "Construction of high copy yeast vectors using 2–μm circle sequences" *Meth Enz* (1983) 101:307–324.
Buchman et al., "The SV40 nucleotide sequence" *DNA Tumor Viruses,* 2nd ed, (J. Tooze, ed.,) Cold Spring Harbor Laboratory, New York (1980), Appendix A, pp. 799–829.
Buckley et al., "Sustained release of epidermal growth factor accelerates wound repair" *Proc Natl Acad Sci USA* (1985) 82:7340–7344.
Burgess et al., "Structural evidence that endothelial cell growth factor β is the precursor of both endothelial cell growth factor α and acidic fibroblast growth factor" *Proc Natl Acad Sci USA* (1986) 83:7216–7220.
Cardin et al., "Binding of a high reactive heparin to human apolipoprotein E: Identification of two heparin–binding domains" *Biochem Biophys Res Comm* (1986) 134:783–789.
Casadaban et al., "Analysis of gene control signals by DNA fusion and cloning in *Escherichia coli*" *J Mol Biol* (1980) 138:179–207.
Clarke et al., "Selection procedure for isolation of centromere DNAs from *Saccharomyces cerevisiae*" *Meth Enz* (1983) 101:300–307.
Clewell et al., "Supercoiled circular DNA–protein complex in *Escherichia coli:* Purification and induced conversion to an open circular DNA form" *Proc Natl Acad Sci USA* (1969) 62:1159–1166.

(List continued on next page.)

Primary Examiner—Christine J. Saoud
(74) Attorney, Agent, or Firm—Burns Doane Swecker & Mathis LLP

(57) ABSTRACT

The DNA sequences encoding analogs of human acidic and basic fibroblast growth factors (FGF) can be recombinantly expressed to obtain practical amounts of proteins useful in effecting both pathologies related to persistent angiogenesis and wound healing and related tissue repair.

6 Claims, 8 Drawing Sheets

OTHER PUBLICATIONS

Clewell, D.B., "Nature of Col E₁ plasmid replication in *Escherichia coli* in the presence of chloramphenicol" *J Bacteriol* (1972) 110:667–676.

Cohen et al., "Nonchromosomal antibiotic resistance in bacteria: Genetic transformation of *Escherichia coli* by R–factor DNA" *Proc Natl Acad Sci USA* (1972) 69:2110–2114.

Davidson et al., Accelerated wound repair, cell proliferation, and collagen accumulation are produced by a cartilage–derived growth factor *J Cell Biol* (1985) 100:1219–1227.

Delbrück et al., "Interference between bacterial viruses. I. Interference between two bacterial viruses acting upon the same host, and the mechanism of virus growth" *Archives of Biochemistry* (1943) 1:111–141.

DeNoto et al., "Human growth hormone DNA sequence and mRNA structure: possible alternative splicing" *Nucleic Acids Res* (1981) 9:3719–3730.

Duckworth et al., "Rapid synthesis of oligodeoxyribonucleotides VI. Efficient, mechanised synthesis of heptadecadeoxyribonucleotides by an improved solid phase phosphotriester route" *Nucleic Acids Res* (1981) 9:1691–1706.

Edge et al., "Total synthesis of a human leukocyte interferon gene" *Nature* (1981) 292:756–762.

Esch et al., Primary structure of bovine brain acidic fibroblast growth factor (FGF) *Biochem Biophys Res Comm* (1985) 133:554–562.

Esch et al., "Primary structure of bovine pituitary basic fibroblast growth factor (FGF) and comparison with the amino–terminal sequence of bovine brain acidic FGF" *Proc Natl Acad Sci (USA)* (1985) 82:6507–6511.

Fiers et al., "Complete nucleotide sequence of SV40 DNA" *Nature* (1978) 273:113–120.

Folkman et al., "Angiogenic factors" *Science* (1987) 235:442–447.

Folkman et al., "Angiogenesis inhibition and tumor regression caused by heparin or a heparin fragment in the presence of cortisone" *Science* (1983) 332:719–725.

Franklin et al., "Effects of topical applications of epidermal growth factor on wound healing" *Plastic and Reconstruc Surg* (1979) 64:766–770.

Gimenez–Gallego et al., "Human brain–derived acidic and basic fibroblast growth factors: Amino terminal sequences and specific mitogenic activities" *Biochem Biophys Res Comm* (1986) 135:541–548.

Gimenez–Gallego et al., "The complete amino acid sequence of human brain–derived acidic fibroblast growth factor" *Biochem Biophys Res. Comm* (1986) 138:611–617.

Gimenez–Gallego et al., "Brain–derived acidic fibroblast growth factor: Complete amino acid sequence and homologies" *Science* (1985) 230:1385–1388.

Goeddel et al., "Synthesis of human fibroblast interferon by *E. coli*" *Nucleic Acids Res* (1980) 8:4057–4074.

Gospodarowicz et al., "Isolation of pituitary fibroblast growth factor by fast protein liquid chromatography (FPLC): Partial chemical and biological characterization" *J Cell Physiol* (1985) 122:323–332.

Gospodarowicz et al., "Isolation of brain fibroblast growth factor by heparin–sepharose affinity chromatography: Identity with pituitary fibroblast growth factor" *Proc Natl Acad Sci USA* (1984) 81:6963–6967.

Gospodarowicz et al., "Fibroblast growth factor in the human placenta" *Biochem Biophys Res Comm* (1985) 128:554–562.

Gospodarowicz et al., "Brain and pituitary fibroblast growth factors" *Hormonal Proteins and Peptides* (1984) XII:205–230 (Academic Press).

Gospodarowicz et al., Bovine brain and pituitary fibroblast growth factors: Comparison of their abilities to support the proliferation of human and bovine vascular endothelial cells: *J Cell Biol* (1983) 97:1677–1685.

Gospodarowicz et al., "Isolation of pituitary fibroblast growth factor by fast protein liquid chromatography (FPLC): Partial chemical and biological characterization" *J Cell Physiol* (1985) 122:323–332.

Gospodarowicz et al., "Effect of fibroblast growth factor and lipoproteins on the proliferation of endothelial cells derived from bovine adrenal cortex, brain cortex, and corpus luteum capillaries" *J Cell Physiol* (1986) 127:121–136.

Gospodarowicz et al., "Isolation and characterization of acidic and basic fibroblast growth factor" *Meth. Enz.* (1987) 147:106–119.

Graham et al., "A new technique for the assay of infecitivity of human adenovirus 5 DNA" *Virology* (1973) 52:456–467.

Gross et al., "Increased capillary endothelial cell protease activity in response to angiogenic stimuli in vitro" *Proc Natl Acad Sci USA* (1983) 80:2623–2627.

Hallewell et al., "Plasmid vectors containing the tryptophan operon promoter suitable for efficient regulated expression of foreign genes" *Gene* (1980) 9:27–47.

Hanahan, D., "Studies on transformation of *Escherichia coli* with plasmids" *J Mol Biol* (1983) 166:557–580.

Harper et al., "Human class 1 heparin–binding growth factor: Structure and homology to bovine acidic brain fibroblast growth factor" *Biochem* (1986) 25:4097–4103.

Hauschka et al., "Growth factors in bone matrix" *J Biol Chem* (1986) 261:12665–12674.

Hess et al., "Cooperation of glycolytic enzymes" *Adv Enzyme Reg* (1968) 7:149–167.

Hinnen et al., "Transformation of yeast" *Proc Natl Acad Sci (USA)* (1978) 75:1929–1933.

Hitzeman et al., "Isolation and characterization of the yeast 3–phosphoglycerokinase gene (PGK) by an immunological screening technique" *J Biol Chem* (1980) 255:12073–12080.

Holland et al., "Isolation and identification of yeast messenger ribonucleic acids coding for enolase, glyceraldehyde–3–phosphate dehydrogenase, and phosphoglycerate kinase" *Biochemistry* (1978) 17:4900–4907.

Holmes et al., "A rapid boiling method for the preparation of bacterial plasmids", *Anal Biochem* (1981) 114:193–197.

Hsieh et al., "Zero–order controlled–release polymer matrices for micro– and macromolecules", *J Pharm Sci* (1983) 72:17–22.

Huang et al., "Bovine brain–derived growth factor" *J Biol Chem* (1986) 261:11600–11607.

Hunt, T.K., "Can repair processes be stimulated by modulators (cell growth factors, angiogenic factors, etc.) without adversely affecting normal processes?" *J. Trauma* (1984) 24:S39–S49.

Ikehara et al., "Synthesis of a gene for human growth hormone and its expression in *Escherichia coli*" *Proc Natl Acad Sci USA* (1984) 81:5956–5960.

Jay et al., "Chemical synthesis of a biologically active gene for human immune interferon–γ" *J Biol Chem* (1984) 259:6311–6317.

Jaye et al., "Human endothelial cell growth factor: Cloning, nucleotide sequence, and chromosome localization" *Science* (1986) 233:541–545.

Kafatos et al., "Determination of nucleic acid sequence homologies and relative concentrations by a dot hybridization procedure" *Nucl Acid Res* (1977) 7:1541–1552.

Karin et al., "Characterization of DNA sequences through which cadmium and glucocorticoid hormones induce human metallothionein–II$_A$ gene" *Nature* (1984) 308:513–519.

Karin et al., "Human metallothionein genes—primary structure of the metallothionein–II gene and a related processed gene" *Nature* (1982) 299:797–802.

Klagsbrun et al., "Heparin affinity of anionic and cationic capillary endothelial cell growth factors: Analysis of hypothalamus–derived growth factors and fibroblast growth factors" *Proc Natl Acad Sci USA* (1985) 82:805–809.

Klagsbrun et al., "Multiple forms of basic fibroblast growth factor: Amino–terminal cleavages by tumor cell– and brain cell–derived acid proteinases" *Proc Natl Acad Sci USA* (1987) 84:1839–1843.

Klagsbrun et al., "Human tumor cells synthesize an endothelial cell growth factor that is structurally related to basic fibroblast growth factor" *Proc Natl Acad Sci USA* (1986) 83:2448–2452.

Laemmli, U.K., "Cleavage of structural proteins during the assembly of the head of bacteriophage T4" *Nature* (1970) 227:680–685.

Langer et al., "Polymers for the sustained release of proteins and other macromolecules" *Nature* (1976) 263:797–799.

Lobb et al., "Purification and characterization of heparin–binding endothelial cell growth factors" *J. Biol. Chem.* (1986) 261:1924–1928.

Lobb et al., "Purification of two distinct growth factors from bovine neural tissue by heparin affinity chromatography" *Biochemistry* (1984) 23:6295–6299.

Maciag et al., "Heparin binds endothelial cell growth factor, the principal endothelial cell mitogen in bovine brain" *Science* (1984) 225:932–935.

Maniatis et al., "Conversion of fragments with protruding 5' ends to blunt ends" (Analysis of Recombinant DNA Clones) *Molecular Cloning: A Laboratory Manual* (1982) Cold Spring Harbor Laboratory, p. 394.

Maniatis et al., "Transformation of *E. coli* $_\chi$1776" (Introduction of Plasmid and Bacteriophage λ DNA Into *Escherichia Coli*) *Molecular Cloning: A Laboratory Manual* (1982) Cold Spring Harbor Laboratory, p. 254.

March et al., "Cloning, sequence and expression of two distinct human interleukin–1 complementary DNAs" *Nature* (1985) 315:641–647.

Mark et al., "Site–specific mutagenesis of the human fibroblast interferon gene" *Proc. Natl. Acad. Sci USA* (1984) 81:5662–5666.

Matteucci et al., "Synthesis of deoxyoligonucleotides on a polymer support" *J Am Chem Soc* (1981) 103:3185–3191.

Maxam et al., "Sequencing end–labeled DNA with base–specific chemical cleavages" *Methods in Enzymology* (1980) 65:499–560.

Messing et al., "A system for shotgun DNA sequencing" *Nucleic Acids Res* (1981) 9:309–321.

Moenner et al., "Evidence and characterization of the receptor to eye–derived growth factor I, the retinal form of basic fibroblast growth factor, on bovine epithelial lens cells" *Proc Natl Acad Sci USA* (1986) 83:5024–5028.

Murray et al., "A micro sustained release system for epidermal growth factor" *In Vitro* (1983) 19:743–748.

Nakamura et al., "Use of a lac promoter–operator fragment as a transcriptional control switch for expression of the constitutive lpp gene in *Escherichia coli*" *J Mol Appl Genet* (1982) 1:289–299.

Nambiar et al., "Total synthesis and cloning of a gene coding for the ribonuclease S protein" *Science* (1984) 223:1299–1301.

Neufeld et al., "The identification and partial characterization of the fibroblast growth factor receptor of baby hamster kidney cells" *J Biol Chem* (1985) 260:13860–13868.

Neufeld et al., "Basic and acidic fibroblast growth factors interact with the same cell surface receptors" *J Biol Chem* (1986) 261:5631–5637.

Olwin et al., "Identification of the fibroblast growth factor receptor of Swiss 3T3 cells and mouse skeletal muscle myoblasts" *Biochemistry* (1986) 25:3487–3492.

Sanger et al., "DNA sequencing with chain–terminating inhibitors" *Proc Natl Acad Sci USA* (1977) 74:5463–5467.

Schubert et al., "Multiple influences of a heparin–binding growth factor on neuronal development" *J Cell Biol* (1987) 104:635–643.

Schwarzbauer et al., "Three different fibronectin mRNAs arise by alternative splicing within the coding region" *Cell* (1983) 35:421–431.

Shimatake et al., "Purified λ regulatory protein cII positively activates promoters for lysogenic development" *Nature* (1981) 292:128–132.

Shing et al., "Heparin affinity: Purification of a tumor––derived capillary endothelial cell growth factor" *Science* (1984) 223:1296–1299.

Smith et al., "Constructed mutants using synthetic oligodeoxyribonucleotides as site–specific mutagens" *Genetic Engineering: Principles and Methods,* Plenum Press (1981) 3:1–32.

Sommer et al., "A form of human basic fibroblast growth factor with an extended amino terminus" *Biochem Biophys Res Comm* (1987) 144:543–550.

Southern et al., "Transformation of mammalian cells to antibiotic resistance with a bacterial gene under control of the SV40 early region promoter" *J Mol Appl Gen* (1982) 1:327–341.

Sporn et al., "Polypeptide transforming growth factors isolated from bovine sources and used for wound healing in vivo" *Science* (1983) 219:1329–1331.

Stinchcomb et al., "Isolation and characterisation of a yeast chromosomal replicator" *Nature* (1979) 282:39–43.

Story et al., "Amino–terminal sequence of a large form of basic fibroblast growth factor isolated from human benign prostatic hyperplastic tissue" *Biochem Biophys Res Comm* (1987) 142:702–709.

Sullivan et al., "A human hepatoma–derived growth factor that stimulates endothelial cell proliferation and angiogenesis: Purification and biosynthesis" *J Cell Biol* (1985) 101:108a (Abstract 409).

Sullivan et al., "Purification of cartilage–derived growth factor by heparin affinity chromatography" *J. Biol. Chem.* (1985) 260:2399–2403.

Svet–Moldavsky et al., "Tumour–angiogenesis factor for revascularisation in ischæmia and myocardial infarction" *Lancet* (Apr. 23, 1977) 913.

Thomas et al., "Pure brain–derived acidic fibroblast growth factor is a potent angiogenic vascular endothelial cell mitogen with sequence homology to interleukin 1" *Proc Natl Acad Sci USA* (1985) 82:6409–6413.

Thomas et al., "Purification and characterization of acidic fibroblast growth factor from bovine brain" *Proc Natl Acad Sci USA* (1984) 81:357–361.

Tschumper et al., "Sequence of a yeast DNA fragment containing a chromosomal replicator and the TRP1 gene" *Gene* (1980) 10:157–166.

Ueno et al., "Isolation of an amino terminal extended form of basic fibroblast growth factor" *Biochem Biophys Res Comm* (1986) 138:580–588.

Vieira et al., "The pUC plasmids, an M13mp7–derived system for insertion mutagenesis and sequencing with synthetic universal primers" *Gene* (1982) 19:259–268.

Walicke et al., "Fibroblast growth factor promotes survival of dissociated hippocampal neurons and enhances neurite extension" *Proc Natl Acad Sci USA* (1986) 83:3012–3016.

Wang et al., "Site–specific mutagenesis of the human interleukin–2 gene: Structure–function analysis of the cysteine residues" *Science* (1984) 224:1431–1433.

Wigler et al., "Transformation of mammalian cells with genes from procaryotes and eucaryotes" *Cell* (1979) 16:777–785.

Zoller et al., "Oligonucleotide–directed mutagenesis using M13–derived vectors: an efficient and general procedure for the production of point mutations in any fragment of DNA" *Nucleic Acids Res* (1982) 10:6487–6500.

\* cited by examiner

FIG. 1-1

Human Basic Fibroblast Growth Factor

```
         10         20         30         40         50         60         70
AATTCATGCC TCTTTCTCTC CTTTTGTTGG TAGACGACTT CAGCCTCTGT CCTTTAATTT TAAAGTTTAT 80         90        100        110        120        130        140
GCCCCACTTG TACCCCTCGT CTTTTGGTGA TTTAGAGATT TTCAAAGCCT GCTCTGACAC AGACTCTTCC 150        160        170        180        190        200        210
TTGGATTGCA ACTTCTCTAC TTTGGGGTGG AAACGGCTTC TCCGTTTTGA AACGCTAGCG GGGAAAAAAT 220        230        240        250        260        270        280
GGGGGAGAAA GTTGAGTTTA AACTTTTAAA AGTTGAGTCA CGGCTGGTTG CGCACGAAAA GCCCCGCAGT 290        300        310        320        330        340        350
GTGGAGAAAG CCTAAACGTG GTTTGGGTGG TGCGGGGGTT GGGCGGGGGT GACTTTTGGG GGATAAGGGG 360        370        380        390        400        410        420
CGGTGGAGCC CAGGGAATGC CAAAGCCCTG CCGCGGCCTC CGACGCGCGC CCCCGCCCC TCGCCTCTCC 430        440        450        460        470        480        490
CCCGCCCCCG ACTGAGGCCG GGCTCCCCGC CGGACTGATG TCGCGCGCTT GCGTGTTGTG GCCGAAGCCG 500        510        520        530        540        550        560
CCGAACTCAG AGGCCGGCCC CAGAAAACCC GAGCGAGTAG GGGGCGGCGC GCAGGAGGGA GGAGAACTGG 570        580        590        600        610        620        630
GGGCGCGGGA GGCTGGTGGG TGTGGGGGGT GGAGATGTAG AAGATGTGAC GCCGCGGCCC GGCGGGTGCC 640        650        660        670        680        690        700
AGATTAGCGG ACGGCTGCCC GCGGTTGCAA CGGGATCCCG GGCGCTGCAG CTTGGGAGGC GGCTCTCCCC 710        720        730        740        750        760        770
AGGCGGCGTC CGCGGAGACA CCCATCTGTG AACCCCAGGT CCCGGGCCGC CGGCTCGCCG CGCACCAGGG 780        790        800        810        820        830        840
GCCGGCGGAC AGAAGAGCGG CCGAGCGGCT CGAGGCTGGG GGACCGCGGG CGCGGCCGCG CGCTGCCGGG 850        860        870        880        890        900        910
CGGGAGGCTG GGGGCCGGG GCCGGGGCCG TGCCCGGAGC GGGTCGGAGG CCGGGGCCGG GGCCGGGGGA 920        930        940        950        960
CGGCGGCTCC CCGCGCGGCT CCAGCGGCTC GGGGATCCCG GCCGGGCCCC GCAGGGACC ATG GCA GCC
                                                                 Met Ala Ala 984                999               1014                1029
GGG AGC ATC ACC ACG CTG CCC GCC TTG CCC GAG GAT GGC GGC AGC GGC GCC TTC CCG
Gly Ser Ile Thr Thr Leu Pro Ala Leu Pro Glu Asp Gly Gly Ser Gly Ala Phe Pro 1044               1059               1074                1089
CCC GGC CAC TTC AAG GAC CCC AAG CGG CTG TAC TGC AAA AAC GGG GGC TTC TTC CTG
Pro Gly His Phe Lys Asp Pro Lys Arg Leu Tyr Cys Lys Asn Gly Gly Phe Phe Leu
```

FIG. 1-2

```
            1104                    1119                    1134                    1149
CGC ATC CAC CCC GAC GGC CGA GTT GAC GGG GTC CGG GAG AAG AGC GAC CCT CAC ATC
Arg Ile His Pro Asp Gly Arg Val Asp Gly Val Arg Glu Lys Ser Asp Pro His Ile 1164                    1179                    1194
AAG CTA CAA CTT CAA GCA GAA GAG AGA GGA GTT GTG TCT ATC AAA GGA GTG TGT GCT
Lys Leu Gln Leu Gln Ala Glu Glu Arg Gly Val Val Ser Ile Lys Gly Val Cys Ala 1224                    1239                    1254
AAC CGT TAC CTG GCT ATG AAG GAA GAT GGA AGA TTA CTG GCT TCT AAA TGT GTT ACG
Asn Arg Tyr Leu Ala Met Lys Glu Asp Gly Arg Leu Leu Ala Ser Lys Cys Val Thr 1269                    1284                    1299                    1314
GAT GAG TGT TTC TTT TTT GAA CGA TTG GAA TCT AAT AAC TAC AAT ACT TAC CGG TCA
Asp Glu Cys Phe Phe Phe Glu Arg Leu Glu Ser Asn Asn Tyr Asn Thr Tyr Arg Ser 1329                    1344                    1359                    1374
AGG AAA TAC ACC AGT TGG TAT GTG GCA TTG AAA CGA ACT GGG CAG TAT AAA CTT GGA
Arg Lys Tyr Thr Ser Trp Tyr Val Ala Leu Lys Arg Thr Gly Gln Tyr Lys Leu Gly 1389                    1404                    1419                    1434
TCC AAA ACA GGA CCT GGG CAG AAA GCT ATA CTT TTT CTT CCA ATG TCT GCT AAG AGC
Ser Lys Thr Gly Pro Gly Gln Lys Ala Ile Leu Phe Leu Pro Met Ser Ala Lys Ser 1450       1460       1470       1480       1490       1500
TGA TTT TAATGGCCAC ATCTAATCTC ATTTCACATG AAAGAAGAAG TATATTTAG AAATTTGTTA 1510       1520       1530       1540       1550       1560       1570
ATGAGAGTAA AAGAAAATAA ATGTGTATAG CTCAGTTTGG ATAATTGGTC AAACAATTTT TTATCCAGTA 1580       1590       1600       1610       1620       1630       1640
GTAAAATATG TAACCATGCC CAGTAAAGAA AAATAACAAA AGTTGTAAAA TGTATATTCT CCCTTTTATA 1650       1660       1670       1680       1690       1700       1710
TTGCATCTGC TGTTACCCAG TGAAGCTTAC CTAGAGCAAT GATCTTTTTC ACGCATTTGC TTTATTCGAA 1720       1730       1740       1750       1760       1770       1780
AAGAGGCTTT TAAAATGTGC ATGTTTAGAA AACAAAATTT CTTCATGGAA ATCATATACA TTAGAAAATC 1790       1800       1810       1820       1830       1840       1850
ACAGTCAGAT GTTTAATCAA TCCAAAAATG TCCACTATTT CTTATGTCAT TCGTTAGTCT ACATGTTTCT 1860       1870       1880       1890       1900       1910       1920
AAACATATAA ATGTGAATTT AATCAATTCC TTTCATAGTT TTATAATTCT CTGGCAGTTC CTTATGATAG 1930       1940       1950       1960       1969
AGTTTATAAA ACAGTCCTGT GTAAACTGCT GGAAGTTCTT CCGGAATTC
```

FIG. 2
Human Acidic FGF

```
                                   27                                                      54
TGC ATT TTG TGC CTT TGC TGG AAG AAC CGA CTA CAG GTT TGT TCA ATT TCT TAC 81                                                                 108
AGT CTT GAA AGC GCC ACA AGC AGC AGC TGC TGA GCC ATG GCT GAA GGG GAA ATC
                                            MET Ala Glu Gly Glu Ile
                                             1

135                                                     162
ACC ACC TTC ACA GCC CTG ACC GAG AAG TTT AAT CTG CCT CCA GGG AAT TAC AAG
Thr Thr Phe Thr Ala Leu Thr Glu Lys Phe Asn Leu Pro Pro Gly Asn Tyr Lys
         10                                                 20

189                                                         216
AAG CCC AAA CTC CTC TAC TGT AGC AAC GGG GGC CAC TTC CTG AGG ATC CTT CCG
Lys Pro Lys Leu Leu Tyr Cys Ser Asn Gly Gly His Phe Leu Arg Ile Leu Pro
                     30                                         40

243                                                     270
GAT GGC ACA GTG GAT GGG ACA AGG GAC AGG AGC GAC CAG CAC ATT CAG CTG CAG
Asp Gly Thr Val Asp Gly Thr Arg Asp Arg Ser Asp Gln His Ile Gln Leu Gln
                             50                                                            60

297                                                     324
CTC AGT GCG GAA AGC GTG GGG GAG GTG TAT ATA AAG AGT ACC GAG ACT GGC CAG
Leu Ser Ala Glu Ser Val Gly Glu Val Tyr Ile Lys Ser Thr Glu Thr Gly Gln
                                         70

351                                                     378
TAC TTG GCC ATG GAC ACC GAC GGG CTT TTA TAC GGC TCA CAG ACA CCA AAT GAG
Tyr Leu Ala MET Asp Thr Asp Gly Leu Leu Tyr Gly Ser Gln Thr Pro Asn Glu
         80                                             90

405                                                     432
GAA TGT TTG TTC CTG GAA AGG CTG GAG GAG AAC CAT TAC AAC ACC TAT ATA TCC
Glu Cys Leu Phe Leu Glu Arg Leu Glu Glu Asn His Tyr Asn Thr Tyr Ile Ser
                 100                                             110

459                                                     486
AAG AAG CAT GCA GAG AAG AAT TGG TTT GTT GGC CTC AAG AAG AAT GGG AGC TGC
Lys Lys His Ala Glu Lys Asn Trp Phe Val Gly Leu Lys Lys Asn Gly Ser Cys
                         120                                             130

513                                                     540
AAA CGC GGT CCT CGG ACT CAC TAT GGC CAG AAA GCA ATC TTG TTT CTC CCC CTG
Lys Arg Gly Pro Arg Thr His Tyr Gly Gln Lys Ala Ile Leu Phe Leu Pro Leu
                                 140                                                      150

567                                                     594
CCA GTC TCT TCT GAT TAA AGA GAT CTG TTC TGG GTG TTG ACC ACT CCA GAG AAG
Pro Val Ser Ser Asp
                 155

621
TTT CGA GGG GTC CTC ACC TGG TTG ACC CAA AAA TGT TCC CTT GA
```

Comparison of amino acid sequence of
human basic and acidic FGF (basic/acidic)

```
        10          20           30            40           50
MAAGSITTLPALPEDGGSGAFPPGHFKDPKRLYCKNGGFFLRIHPDGRVDGVREKSDPHI
:: ::        :  ::   :::  ::  ::::::::: ::::: :::::::  ::
MAEGEITTFTALTEKFNL---PPGNYKKPKLLYCSNGGHFLRILPDGTVDGTRDRSDQHI
        10           20           30           40           50

70           80           90          100           110         120
KLQLQAEERGVVSIKGVCANRYLAMKEDGRLLASKCVTDECFFFERLESNNYNTYRSRKY
:::::::::: ::::::::: :::: ::::: ::::::::::::::::::::::::: ::
QLQLSAESVGEVYIKSTETGQYLAMDTDGLLYGSQTPNEECLFLERLEENHYNTYISKKH
        70           80           90          100           110

130        140             150
TS--WYVALKRTGQYKLGSKTGPGQKAILFLPMSAKS
:    :::::   :::::  ::::::::::::   :
AEKNWFVGLKKNGSCKRGPRTHYGQKAILFLPLPVSSD
        120          130         140         150
```

Heparin binding domain → Receptor binding domain →

→ Receptor binding domain   Heparin binding domain

← Heparin binding domain

FIG. 3

SEQUENCE LISTING (1) GENERAL INFORMATION:

(iii) NUMBER OF SEQUENCES: 69

(2) INFORMATION FOR SEQ ID NO:1:

(i) SEQUENCE CHARACTERISTICS:
       (A) LENGTH: 1969 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: Coding Sequence
       (B) LOCATION: 970...1434
       (D) OTHER INFORMATION:

(xi) SEQUENCE DESCRIPTION: SEQ ID NO:1:

```
AATTCATGCC TCTTTCTCTC CTTTTGTTGG TAGACGACTT CAGCCTCTGT CCTTTAATTT      60

TAAAGTTTAT GCCCCACTTG TACCCCTCGT CTTTTGGTGA TTTAGAGATT TTCAAAGCCT     120

GCTCTGACAC AGACTCTTCC TTGGATTGCA ACTTCTCTAC TTTGGGGTGG AAACGGCTTC     180

TCCGTTTTGA AACGCTAGCG GGGAAAAAAT GGGGGAGAAA GTTGAGTTTA AACTTTTAAA     240

AGTTGAGTCA CGGCTGGTTG CGCACGAAAA GCCCCGCAGT GTGGAGAAAG CCTAAACGTG     300

GTTTGGGTGG TGCGGGGGTT GGGCGGGGGT GACTTTTGGG GGATAAGGGG CGGTGGAGCC     360

CAGGGAATGC CAAAGCCCTG CCGCGGCCTC CGACGCGCGC CCCCCGCCCC TCGCCTCTCC     420

CCCGCCCCCG ACTGAGGCCG GGCTCCCCGC CGGACTGATG TCGCGCGCTT GCGTGTTGTG     480

GCCGAAGCCG CCGAACTCAG AGGCCGGCCC CAGAAAACCC GAGCGAGTAG GGGGCGGCGC     540

GCAGGAGGGA GGAGAACTGG GGGCGCGGGA GGCTGGTGGG TGTGGGGGGT GGAGATGTAG     600

AAGATGTGAC GCCGCGGCCC GGCGGGTGCC AGATTAGCGG ACGGCTGCCC GCGGTTGCAA     660

CGGGATCCCG GGCGCTGCAG CTTGGGAGGC GGCTCTCCCC AGGCGGCGTC CGCGGAGACA     720

CCCATCTGTG AACCCCAGGT CCCGGGCCGC CGGCTCGCCG CGCACCAGGG GCCGGCGGAC     780

AGAAGAGCGG CCGAGCGGCT CGAGGCTGGG GGACCGCGGG CGCGGCCGCG CGCTGCCGGG     840

CGGGAGGCTG GGGGGCCGGG GCCGGGGCCG TGCCCGGAGC GGGTCGGAGG CCGGGGCCGG     900

GGCCGGGGGA CGGCGGCTCC CCGCGCGGCT CCAGCGGCTC GGGGATCCCG GCCGGGCCCC     960

GCAGGGACC ATG GCA GCC GGG AGC ATC ACC ACG CTG CCC GCC TTG CCC GAG    1011
          Met Ala Ala Gly Ser Ile Thr Thr Leu Pro Ala Leu Pro Glu
            1               5                  10

GAT GGC GGC AGC GGC GCC TTC CCG CCC GGC CAC TTC AAG GAC CCC AAG       1059
Asp Gly Gly Ser Gly Ala Phe Pro Pro Gly His Phe Lys Asp Pro Lys
 15              20                  25                  30

CGG CTG TAC TGC AAA AAC GGG GGC TTC TTC CTG CGC ATC CAC CCC GAC       1107
Arg Leu Tyr Cys Lys Asn Gly Gly Phe Phe Leu Arg Ile His Pro Asp
                 35                  40                  45

GGC CGA GTT GAC GGG GTC CGG GAG AAG AGC GAC CCT CAC ATC AAG CTA       1155
Gly Arg Val Asp Gly Val Arg Glu Lys Ser Asp Pro His Ile Lys Leu
             50                  55                  60

CAA CTT CAA GCA GAA GAG AGA GGA GTT GTG TCT ATC AAA GGA GTG TGT       1203
Gln Leu Gln Ala Glu Glu Arg Gly Val Val Ser Ile Lys Gly Val Cys
 65                  70                  75
```

```
GCT AAC CGT TAC CTG GCT ATG AAG GAA GAT GGA AGA TTA CTG GCT TCT      1251
Ala Asn Arg Tyr Leu Ala Met Lys Glu Asp Gly Arg Leu Leu Ala Ser
         80              85                  90

AAA TGT GTT ACG GAT GAG TGT TTC TTT TTT GAA CGA TTG GAA TCT AAT      1299
Lys Cys Val Thr Asp Glu Cys Phe Phe Phe Glu Arg Leu Glu Ser Asn
 95              100                 105                 110

AAC TAC AAT ACT TAC CGG TCA AGG AAA TAC ACC AGT TGG TAT GTG GCA      1347
Asn Tyr Asn Thr Tyr Arg Ser Arg Lys Tyr Thr Ser Trp Tyr Val Ala
                 115                 120                 125

TTG AAA CGA ACT GGG CAG TAT AAA CTT GGA TCC AAA ACA GGA CCT GGG      1395
Leu Lys Arg Thr Gly Gln Tyr Lys Leu Gly Ser Lys Thr Gly Pro Gly
         130                 135                 140

CAG AAA GCT ATA CTT TTT CTT CCA ATG TCT GCT AAG AGC TGATTTTAAT GG    1446
Gln Lys Ala Ile Leu Phe Leu Pro Met Ser Ala Lys Ser
             145                 150                 155

CCACATCTAA TCTCATTTCA CATGAAAGAA GAAGTATATT TTAGAAATTT GTTAATGAGA    1506

GTAAAAGAAA ATAAATGTGT ATAGCTCAGT TTGGATAATT GGTCAAACAA TTTTTTATCC    1566

AGTAGTAAAA TATGTAACCA TGCCCAGTAA AGAAAAATAA CAAAAGTTGT AAAATGTATA    1626

TTCTCCCTTT TATATTGCAT CTGCTGTTAC CCAGTGAAGC TTACCTAGAG CAATGATCTT    1686

TTTCACGCAT TTGCTTTATT CGAAAAGAGG CTTTTAAAAT GTGCATGTTT AGAAAACAAA    1746

ATTTCTTCAT GGAAATCATA TACATTAGAA AATCACAGTC AGATGTTTAA TCAATCCAAA    1806

AATGTCCACT ATTTCTTATG TCATTCGTTA GTCTACATGT TTCTAAACAT ATAAATGTGA    1866

ATTTAATCAA TTCCTTTCAT AGTTTTATAA TTCTCTGGCA GTTCCTTATG ATAGAGTTTA    1926

TAAAACAGTC CTGTGTAAAC TGCTGGAAGT TCTTCCGGAA TTC                      1969

(2) INFORMATION FOR SEQ ID NO:2:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
             20                  25                  30

Tyr Cys Lys Asn Gly Gly Phe Phe Leu Arg Ile His Pro Asp Gly Arg
         35                  40                  45

Val Asp Gly Val Arg Glu Lys Ser Asp Pro His Ile Lys Leu Gln Leu
     50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
             100                 105                 110

Asn Thr Tyr Arg Ser Arg Lys Tyr Thr Ser Trp Tyr Val Ala Leu Lys
         115                 120                 125
```

```
Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

(2) INFORMATION FOR SEQ ID NO:3:

(i) SEQUENCE CHARACTERISTICS:
        (A) LENGTH: 638 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 91...555
        (D) OTHER INFORMATION:

(xi) SEQUENCE DESCRIPTION: SEQ ID NO:3:

```
TGCATTTTGT GCCTTTGCTG GAAGAACCGA CTACAGGTTT GTTCAATTTC TTACAGTCTT        60

GAAAGCGCCA CAAGCAGCAG CTGCTGAGCC  ATG GCT GAA GGG GAA ATC ACC ACC       114
                                 Met Ala Glu Gly Glu Ile Thr Thr
                                  1               5

TTC ACA GCC CTG ACC GAG AAG TTT AAT CTG CCT CCA GGG AAT TAC AAG         162
Phe Thr Ala Leu Thr Glu Lys Phe Asn Leu Pro Pro Gly Asn Tyr Lys
        10                  15                  20

AAG CCC AAA CTC CTC TAC TGT AGC AAC GGG GGC CAC TTC CTG AGG ATC         210
Lys Pro Lys Leu Leu Tyr Cys Ser Asn Gly Gly His Phe Leu Arg Ile
25                  30                  35                  40

CTT CCG GAT GGC ACA GTG GAT GGG ACA AGG GAC AGG AGC GAC CAG CAC         258
Leu Pro Asp Gly Thr Val Asp Gly Thr Arg Asp Arg Ser Asp Gln His
                45                  50                  55

ATT CAG CTG CAG CTC AGT GCG GAA AGC GTG GGG GAG GTG TAT ATA AAG         306
Ile Gln Leu Gln Leu Ser Ala Glu Ser Val Gly Glu Val Tyr Ile Lys
            60                  65                  70

AGT ACC GAG ACT GGC CAG TAC TTG GCC ATG GAC ACC GAC GGG CTT TTA         354
Ser Thr Glu Thr Gly Gln Tyr Leu Ala Met Asp Thr Asp Gly Leu Leu
        75                  80                  85

TAC GGC TCA CAG ACA CCA AAT GAG GAA TGT TTG TTC CTG GAA AGG CTG         402
Tyr Gly Ser Gln Thr Pro Asn Glu Glu Cys Leu Phe Leu Glu Arg Leu
    90                  95                  100

GAG GAG AAC CAT TAC AAC ACC TAT ATA TCC AAG AAG CAT GCA GAG AAG         450
Glu Glu Asn His Tyr Asn Thr Tyr Ile Ser Lys Lys His Ala Glu Lys
105                 110                 115                 120

AAT TGG TTT GTT GGC CTC AAG AAG AAT GGG AGC TGC AAA CGC GGT CCT         498
Asn Trp Phe Val Gly Leu Lys Lys Asn Gly Ser Cys Lys Arg Gly Pro
                125                 130                 135

CGG ACT CAC TAT GGC CAG AAA GCA ATC TTG TTT CTC CCC CTG CCA GTC         546
Arg Thr His Tyr Gly Gln Lys Ala Ile Leu Phe Leu Pro Leu Pro Val
            140                 145                 150

TCT TCT GAT TAAAGAGATC TGTTCTGGGT GTTGACCACT CCAGAGAAGT TTCGAGGGG       604
Ser Ser Asp
        155

TCCTCACCTG GTTGACCCAA AAATGTTCCC TTGA                                    638
```

(2) INFORMATION FOR SEQ ID NO:4:

(i) SEQUENCE CHARACTERISTICS:
        (A) LENGTH: 155 amino acids
        (B) TYPE: amino acid (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

(2) INFORMATION FOR SEQ ID NO:5:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (xi) SEQUENCE DESCRIPTION: SEQ ID NO:5:

AGAATTCAAA TATTCTGAAA TGAGCTGTTG ACAATTAATC ATCGAACTAG TTAACTAGTA      60

CGCAAGTTCA CGTAAAAAGG GTATCACATA TGGTACCTGC AGA                       103

(2) INFORMATION FOR SEQ ID NO:6:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (xi) SEQUENCE DESCRIPTION: SEQ ID NO:6:

TCTGCAGGTA CCATATGTGA TACCCTTTTT ACGTGAACTT GCGTACTAGT TAACTAGTTC      60

GATGATTAAT TGTCAACAGC TCATTTCAGA ATATTTGAAT TCT                       103

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear -continued (xi) SEQUENCE DESCRIPTION: SEQ ID NO:7:

GAAATACACC AGTTGG                                                       16

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

ACTTGGATCC AAAACAG                                                      17

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:9:

TTTTACATGA AGCTTTATAT TTCAG                                             25

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:10:

AGCTTCATAT GGCTGCTGGT TCTATCACTA CC                                     32

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:11:

CTGCCAGCTC TGCCAGAAGA CGGTGGTT                                          28

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

CTGGTGCCTT CCCACCAGGT CACTTCAA                                          28

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:13:

AGACCCAAAA CGTCTGTACT GCAAAAAC                                              28

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:14:

GGTGGTTTCT TCCTGCGCA                                                        19

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

TAGAACCAGC AGCCATATGA                                                       20

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

TCTTCTGGCA GAGCTGGCAG GGTAGTGA                                              28

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

ACCTGGTGGG AAGGCACCAG AACCACCG                                              28

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:18:

AGTACAGACG TTTTGGGTCT TTGAAGTG                                              28

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:19:

AGCTTGCGCA GGAAGAAACC ACCGTTTTTG C                                            31

(2) INFORMATION FOR SEQ ID NO:20:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO:20:

AGCTTCATAT GGCTGCTGGT TCTATCACTA CCCTGCCAGC TCTGCCAGAA GACGGTGGTT            60

CTGGTGCCTT CCCACCAGGT CACTTCAAAG ACCCAAAACG TCTGTACTGC AAAAACGGTG           120

GTTTCTTCCT GCGCA                                                            135

(2) INFORMATION FOR SEQ ID NO:21:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (xi) SEQUENCE DESCRIPTION: SEQ ID NO:21:

AGCTTGCGCA GGAAGAAACC ACCGTTTTTG CAGTACAGAC GTTTTGGGTC TTTGAAGTGA            60

CCTGGTGGGA AGGCACCAGA ACCACCGTCT TCTGGCAGAG CTGGCAGGGT AGTGATAGAA           120

CCAGCAGCCA TATGA                                                            135

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:22:

ACGTCTGTAC TCCAAAAACG GTG                                                    23

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:23:

TACAGACGAG TCTTTCTTTT TTG                                                    23

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:24:

CAAAGGAGTG TCTGCAAACC GTT                                                    23

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:25:

AGCTTCTAAA TCTGTTACAG ACG                                      23

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:26:

ACGTCTGTAC TCCAAAAACG GTG                                      23

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:27:

TACAGACGAG TCTTTCTTTT TTG                                      23

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:28:

GTCTGTACTG CTCAAACGGT GGTT                                   24

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:29:

TTTCTTCCTG CTCATCCACC CCG                                      23

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:30:

CATCCACCCC GCCGGCCGAG TGG                                      23

(2) INFORMATION FOR SEQ ID NO:31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:31:

CCCCGACGGC CTAGTGGACG GGG                                    23

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:32:

ACCCCGACGG CGCAGTGGAC GGGG                                   24

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:33:

CGGCCGGAGT GGCCGGGGTC CGCG                                   24

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:34:

GAGTGGACGG GAAACGCGAG AAGAG                                 25

(2) INFORMATION FOR SEQ ID NO:35:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:35:

GGACGGGGTC CTCGAGAAGA GCG                                    23

(2) INFORMATION FOR SEQ ID NO:36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:36:

GGTCCGCGAG ATGAGCGACC CAC                                    23

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:37:

GGTCCGCGAG ATAAGCGACC CACA        24

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:38:

CGAGAAGAGC GCCCCACACA TCA        23

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:39:

GAGCGACCCA AACATCAAAC TAC        23

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:40:

AGAAGATGGA ACTTTACTAG CTTC        24

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:41:

ATGTGTTACA GCAGAGTGTT TCT        23

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:42:

GTTACAGACG CCTGTTTCTT TTTTG        25

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:43:

GTGTTACAGA CAGTTGTTTC TTTTT        25

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:44:

GTTTCTTTTT TTCACGATTG GAGT        24

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:45:

CTTTTTTGAA CTATTGGAGT CTA        23

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:46:

TGAACGATTG GCATCTAATA ACTA        24

(2) INFORMATION FOR SEQ ID NO:47:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:47:

AGTCTAATAA CGCAAATACT TACCG        25

(2) INFORMATION FOR SEQ ID NO:48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:48:

CTAATAACTA CAGTACTTAC CGG        23

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:49:

CAATACTTAC ACTTCAAGGA AATA                                          24

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:50:

CAATACTTAC CTGTCAAGGA AAT                                           23

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:51:

ACCGGTCAAG GTCTTACACC AGTTG                                     25

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:52:

GGTGGTTTCT TCCACCCCGA CGGC                                          24

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:53:

CCCGACGGCC GAGTCCGCGA GAAG                                          24

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:54:

CCACACATCA AACAAGCAGA AGAG                                          24

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:55:

GCAAACCGTT ACAAAGAAGA TGGA    24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:56:

TGTTTCTTTT TTGAGTCTAA TAAC    24

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:57:

GAGTCTAATA ACTACCGGTC AAGG    24

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:58:

AGGTCACTTC ATGGACCCAA AACG    24

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:59:

TCAAAGACCC AGCACGTCTG TACT    24

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:60:

AAGACCCAAA ATCTCTGTAC TGCA    24

(2) INFORMATION FOR SEQ ID NO:61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:61:

GTCACTTCAA AAAGCCAAAA CGTCT                                             25

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:62:

CAATACTTAC CTGTCAAGGA AAT                                               23

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:63:

GTCTGTACTG CTCAAACGGT GGTT                                              24

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:64:

ATGTGGCACT GTCTCGAACT GGGCA                                             25

(2) INFORMATION FOR SEQ ID NO:65:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:65:

ATGTGGCACT GGAGCGAACT GGGCA                                             25

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:66:

GGCACTGAAA ACTACTGGGC AGT                                               23

(2) INFORMATION FOR SEQ ID NO:67:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:67:

CTGGGCAGTA TTCTCTTGGA TCCAA                                             25

(2) INFORMATION FOR SEQ ID NO:68:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:68:

AACTTGGATC CTCTACAGGA CCTGG                                             25

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

TTGGGTCTTT GAAGTGCATA TGTGGGAAGG CACCAG                                 36

HUMAN BASIC FIBROBLAST GROWTH FACTOR ANALOG

CROSS-REFERENCE TO RELATED APPLICATION

This is a divisonal of U.S. Ser. No. 07/459,739, Feb. 12, 1990, now U.S. Pat. No. 5,859,208, which is a continuation-in-part of U.S. Ser. No. 07/070,797, filed Jul. 7, 1987, now abandoned, which is a continuation-in-part of U.S. Ser. No. 07/050,706, filed May 15, 1987, now abandoned, which is a continuation-in-part of U.S. Ser. No. 06/869,382 filed May 30, 1986, now abandoned, which is a continuation-in-part of U.S. Ser. No. 06/809,163, filed Dec. 16, 1985, now U.S. Pat. No. 5,439,818 which is a continuation-in-part of U.S. Ser. No. 06/775,521, filed Sep. 12, 1985, now abandoned.

TECHNICAL FIELD

The invention relates to recombinant production of growth factors important for constructing vascular systems in healing tissues and inhibiting abnormal persistent angiogenesis. In particular, analogs of genes encoding human basic and acidic fibroblast growth factors (FGF) are cloned and expressed.

BACKGROUND ART

The process of healing when tissue is subjected to trauma, such as wounding or burns, is an extremely complex one, but it is known to be mediated by a number of protein factors. These factors are essential to the growth and differentiation of the cells which serve to replace the tissue destroyed. A number of candidate factors have been identified on the basis of the ability of extracts from various tissues, such as brain, pituitary, and hypothalamus, to stimulate the mitosis of cultured cells. Numerous shorthand names have been applied to the active factors in these extracts, including platelet-derived growth factor (PDGF), macrophage-derived growth factor (MDGF), epidermal growth factor (EGF), tumor angiogenesis factor (TAF), endothelial cell growth factor (ECGF), fibroblast growth factor (FGF), hypothalamus-derived growth factor (HDGF), retina-derived growth factor (RDGF), and heparin-binding growth factor (HGF). (See, for example, Hunt, T. K., *J Trauma* (1984) 24:S39–S49; Lobb, R. R., et al, *Biochemistry* (1984) 23:6295–6299).

Folkman, J., et al, *Science* (1983) 221:719–725, reported that one of the processes involved in wound healing, the formation of blood vessels, is profoundly affected in tumors by heparin. From this and other studies, it is clear that heparin specifically binds to protein(s) associated with a number of these growth factor activities, and therefore heparin has been used as a purification tool. It has been shown that the affinity of some growth factors for heparin is independent of overall ionic charge, since both positively and negatively charged factors are bound (Maciag, T., et al, *Science* (1984) 225:932–935;Shing, Y., et al, *Science* (1984) 223:1296–1299; Klagsbrun, M., et al, *Proc Natl Acad Sci (USA)* (1985) 82:805–809). The capacity to bind or not to bind to heparin is one measure of differentiation between the activities in the various extracts. For example, EGF and PDGF do not bind strongly to heparin; in fact, EGF does not bind to heparin at all. The other factors above do show strong heparin binding. However, it is believed that acidic brain FGF, ECGF, RDGF, and HGF-alpha are in fact the same factor. Similarly, it is also believed that pituitary FGF, cationic brain FGF, TAF, and HGF- are the same protein. (Lobb, R. R., et al (supra)). A summary and comparison of thirteen endothelial growth factors which have been purified using heparin affinity is found in Lobb, R., et al, *J Biol Chem* (1986) 261:1924–1928.

Using heparin affinity chromatography, basic fibroblast growth factors exhibiting a potent mitogenic activity for capillary endothelium have been isolated from rat chondrosarcoma (Shing, Y., et al, supra) and from bovine cartilage (Sullivan, R., et al, *J Biol Chem* (1985) 260:2399–2403). Thomas, K. A, et al, *Proc Natl Acad Sci (USA)* (1984) 81:357–361, U.S. Pat. No. 4,444,760, purified two heterogeneous forms of an acidic bovine brain fibroblast growth factor having molecular weights of 16,600 and 16,800 daltons. Gospodarowicz and collaborators have shown the presence in both bovine brains and pituitaries of basic fibroblast growth factor activities and purified these proteins using heparin-affinity chromatography in combination with other purification techniques (Bohlen, P., et al, *Proc Natl Acad Sci (USA)* (1984) 81:5364–5368; Gospodarowicz, D., et al (ibid) 6963–6967). These factors also have molecular weights of approximately 16 kd, as does a similar factor isolated from human placenta (Gospodarowicz, D., et al, *Biochem Biophys Res Comm* (1985) 128:554–562).

The complete sequence for basic FGF derived from bovine pituitary has been determined (Esch, F., et al, *Proc Natl Acad Sci (USA)* (1985) 82: 6507–6511). Homogeneous preparations were obtained and showed potent mitogenic activity in in vitro assays with endothelial cells (basic FGF has an $ED_{50}$ of 60 pg/ml).

Acidic FGF has an $ED_{50}$ of about 6,000 pg/ml. An N-terminal sequence for acidic FGF derived from bovine brain tissue was determined by Bohlen, P., et al, *EMBO J* (1985) 4:1951–1956. Gimenez-Gallego, G., et al, determined the N-terminal sequences for both acidic and basic FGF prepared from human brain, and compared them to the bovine sequences (*Biochem Biophys Res Comm* (1986) 135:541–548). Their results are consistent with those disclosed herein. Also, the complete amino acid sequence of bovine brain-derived acidic FGF was determined from the isolated protein (Gimenez-Gallego, G., et al, *Science* (1985) 230:1385–1388; Esch, F., et al, *Biochem Biophys Res Comm* (1985) 133:554–562). These two determinations are in agreement with the exception of a single amino acid. However, Esch et al later reported that their sequence is in agreement with that of Gimenez-Gallego et al. The complete amino acid sequence of human acidic FGF was deduced from the gene (Jaye, M., et al, *Science* (1986) 233:541–545 and the complete human protein sequence was also determined by Gimenez-Gallego, G., et al, *Biochem Biophys Res Comm* (1986) 138:611–617 and Harper, J. W., et al, *Biochem* (1986) 25:4097–4103).

The FGF proteins described above and other growth factors are clearly effective in promoting the healing of tissue subjected to trauma (see, e.g., Sporn, M. B., et al, *Science* (1983) 219:1329–1331; Davidson, J. M., et al, J.C.B. (1985) 100:1219–1227; Thomas, K. A., et al, *Proc Natl Acad Sci (USA)* (1985) 82:6409–6413). Davidson, et al, (supra) specifically discloses the efficacy of FGF in wound healing. The basic FGF native proteins have been alleged to be useful in treatment of myocardial infarction (Svet-Moldavsky, G. J., et al, *Lancet* (Apr. 23, 1977) 913; U.S. Pat. Nos. 4,296,100 and 4,378,347). In addition, human basic FGF has been found to increase neuronal survival and neurite extension in fetal rat hippocampal neurons (Walicke, P., et al, *Proc Natl Acad Sci (USA)* (1986) 83:3012–3016), suggesting that this factor may also be useful in the treatment of degenerative neurological disorders, such as Alzheimer's disease and Parkinson's disease.

The FGF proteins described above provide an effective means to promote the repair of traumatized tissue as a result of wounding, surgery, burns, fractures or neurological degeneration. However, data is accumulating regarding certain properties of these growth factors which suggests that agonists of FGF may be more therapeutically effective than the native FGF proteins for tissue repair, and in certain circumstances that FGF antagonists may also be useful therapeutically.

For example, agonists of FGF which have greater biological activity as compared to native FGF would be more desirable for use in the wound healing indications described above. In contrast, antagonists of FGF would be extremely useful in therapies where neovascularization is a dominant pathology and it would be therapeutically useful to inhibit the process of angiogenesis. Therefore, it would also be desirable to construct FGF analogs which antagonize the effects of native FGF thereby inhibiting angiogenesis.

It is considered desirable to provide modifications to the native FGF DNA sequences reported for these growth factors in order to isolate the regions of the protein responsible for the distinct biological activities or regions important in the interactions of the factor with the cellular environment. Having determined the appropriate region or site of the specific interaction, structural analogs can be created which preserve certain activities, e.g. wound healing activity, while reducing or eliminating undesirable functions, such as the sequestration of FGF in the extracellular matrix.

It would also be desirable to insure the availability of these FGF protein analogs in large quantities and in a form free from any toxic or infectious impurities. The human form of the protein is preferred, and perhaps required, for therapeutic use. Since the DNA sequences encoding the proteins for both human acidic and basic FGF have been cloned and expressed by recombinant DNA techniques, site-directed mutagenesis may be employed to produce a variety of acidic and basic FGF analogs. The invention herein provides the means whereby acidic and basic FGF analogs can be obtained in practical quantities and in pure, uncontaminated form.

DISCLOSURE OF THE INVENTION

The invention provides the tools for synthesis and manipulation of fibroblast growth factor analogs useful in effecting accelerated healing of wounds, bone fractures, burn tissue, damaged myocardial tissue, degenerated neurological tissue, or other trauma. Concurrently, fibroblast growth factor antagonists, such as angiogenesis inhibitors, which would be useful for treatment of diseases common to ophthalmology, dermatology and rheumatology where neovascularization is a dominant pathology, and in certain neoplasms that include, but are not limited to, the most highly angiogenic, such as brain tumors, are also provided. Cloning and expression of the genes encoding these analogs are provided by the methods and materials of the invention.

In one aspect, the invention relates to recombinant DNA sequences encoding analogs of human acidic and basic FGF (human aFGF and human bFGF). In other aspects, the invention relates to recombinant vectors bearing these DNA sequences, to host cells transformed with such vectors and harboring these DNA sequences, and to the recombinant proteins produced by these transformed cells. In yet other aspects, the invention relates to methods of producing these fibroblast growth factor analogs using recombinant techniques.

BRIEF DESCRIPTION OF THE DRAWINGS

FIGS. 1 and 2 show the native DNA sequences encoding, and the deduced amino acid sequences of, human basic FGF (SEQ ID NO: 1) and acidic FGF (SEQ ID NO: 3), respectively.

FIG. 3 shows a comparison of the amino acid sequences for human acidic (SEQ ID NO: 4) and basic (SEQ ID NO: 2) FGF and the various regions targeted for alteration, including potential heparin-binding domains and receptor-binding regions.

FIG. 7 shows the elution of 10 ug of reduced (FIG. 7a) and nonreduced (FIG. 7b) bFGF-C78/96S from a heparin HPLC column developed with a NaCl gradient (0.6 M–3.0 M). A similar experiment using purified wild type bFGF under reduced (FIG. 7c) and nonreduced (FIG. 7d) conditions is provided for comparison.

MODES OF CARRYING OUT THE INVENTION

A. The Fibroblast Growth Factors

Figure 4:
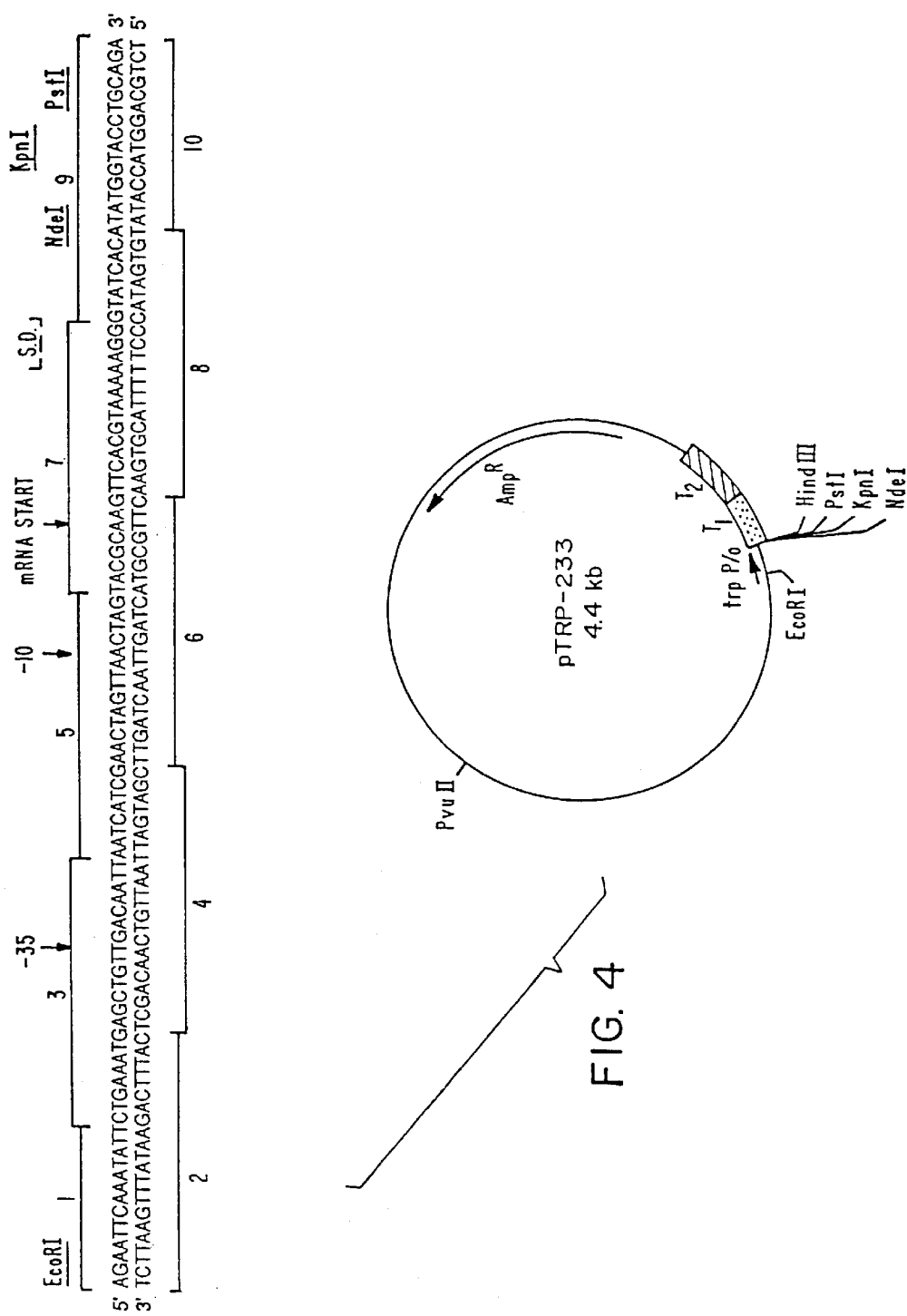
FIG. 4 shows the construction of a synthetic tryptophan operon promoter and operator regulatory sequence (SEQ ID NO: 5–6), and a restriction site map of plasmid pTRP-233.

Two different bovine (and analogous human) fibroblast growth factors have been purified to homogeneity by others and partially or completely sequenced. Both factors are capable of mitogenic activity in in vitro assays using cultured cells, such as bovine brain and adrenal cortex-derived capillary endothelial cells, human umbilical vein endothelial cells, bovine adrenal cortex steroidogenic cells, granulosa cells, and vascular smooth muscle cells. In vitro assays employing these cell cultures have been described by Gospodarowicz, D., et al, *J Cell Physiol* (1985) 122:323–332; and Gospodarowicz, D., et al, *J Cell Biol* (1983) 97:1677–1685. More recently, alternative in vitro assays have been described by Esch et al, *Proc Natl Acad Sci (USA)* (1985) 82:6507–6511; and by Gospodarowicz, D., et al, *J Cell Physiol* (1986) 127: 121–136. Purified bovine basic FGF has been shown to be angiogenic in vivo in a chicken chorioallantoic membrane assay. (Gospodarowicz, D. in *Hormonal Proteins and Peptides XII*:205–230 (Academic Press). Purified bovine acidic FGF has been shown to be angiogenic in vivo in the same assay (Thomas, K. A., et al, *Proc Natl Acad Sci* (supra)).

Bovine pituitary basic FGF has been completely sequenced by Esch, *Proc Natl Acad Sci USA* (supra); the human sequence is shown in FIG. 1. The reported primary sequence contains 146 amino acids, beginning with the proline residue numbered "10" in FIG. 1; the N-terminal portion of this sequence is in agreement with the sequence previously reported for the N-terminus of the native bovine protein by Bohlen et al, *Proc Natl Acad Sci USA* (supra). A higher molecular weight human basic FGF has been reported from the human hepatoma cell line, SK-HEP-1, by Sullivan, R. J., et al, *J Cell Biol* (1985) 101:108a; by Klagsbrun, M., et al, *Proc Natl Acad Sci USA* (1986)

83:2448–2452; and by Klagsbrun, M. et al, *Proc Natl Acad Sci USA* (1987) 84:1839–1843. Longer forms of FGF have been reported by Sommer, A., et al, *Biochem Biophys Res Comm* (1987) 144:543 (human placental tissue) as well as from pituitary and human prostatic tissue reported by Uneo, et al, *Biochem Biophys Res Comm* (1986) 138:580–588 and Story, et al, *Biochem-Biophys Res Comm* (1987) 142:702–709, respectively. Translation of the upstream sequences of FIG. 1 back to a potential ATG translation start codon in human basic FGF DNA shows that it is likely that an additional form of the protein containing the amino acids upstream of the proline shown as residue 10 in FIG. 1 is also produced. The ATG codon lies nine codons upstream from the codon for the proline residue. It is reasonably certain that if the methionine encoded by this ATG serves as the initiating methionine, then it will be processed off when the gene is expressed in eucaryotic systems. Such processing may or may not occur when the gene is expressed recombinantly in bacterial systems. Thus, the "long" form of the protein expressed in bacteria contains an additional 8 or 9 amino acid sequence at the N-terminus, for a total of 154 or 155 amino acids. All of the investigative groups have also shown that much of this extended FGF is blocked at the N-terminus.

Proteins having FGF activity in the above-mentioned in vitro assays and sharing a similar putative N-terminal sequence with the bovine pituitary basic FGF (the 146 amino acid form) have also been isolated from bovine brain, adrenal gland, retina, and from human placenta. The native protein obtained from certain of these tissues is heterogeneous—a second form missing the putative fifteen N-terminal amino acids retains activity. (Gospodarowicz, D., *Meth Enz* (1987) 147A:106–119.) It is considered, therefore, that bovine and human basic FGFs exist in at least three forms, a mature form starting at amino acid 10 in FIG. 1 (a proline), longer forms containing eight additional amino acids at the N-terminus, and shorter forms lacking fifteen amino acids of the putative mature sequences shown. Thus, there is believed to be natively produced "long" basic FGF containing 154 or 155 amino acids (Abraham, J. A., et al, *EMBO J* (1986) 5:2523–2528), "primary" basic FGF containing 146 amino acids, and "short" basic FGF containing 131 amino acids. It is also possible that forms extending even further upstream exist. These FGFs are designated "basic" FGF, because they contain a high number of basic amino acid residues (lysine, arginine, histidine) and are therefore cations at neutral pH.

A protein is defined herein as basic FGF (also referred to as bFGF) if it shows FGF activity in the foregoing assays, binds to heparin, is a cation at neutral pH, and reacts immunologically with antibodies prepared using a synthetic analog of the amino terminal sequence [tyr$^{10}$] FGF (1–10) conjugated to bovine serum albumin (if appropriate) or to other antibodies raised against bovine (or human) FGF or synthetic or native peptides thereof. See Baird, A., et al, *Regulatory Peptides* (1985) 10:309–317.

Acidic FGF has been isolated from bovine and human brain by others, and the complete coding sequence for human acidic FGF was determined and is shown in FIG. 2.

The acidic protein also has three known active forms, one having the 140 amino acid sequence beginning at the phenylalanine residue numbered "16" in the figure, and a second shorter form corresponding to amino acids 22–155, and an N-terminal extended form corresponding to 2–155 (blocked by acetylation) Burgess, et al, *Proc Natl Acad Sci USA* (1986) 83:7216. These proteins contain a disproportionate number of acidic amino acid residues, i.e., glutamic and aspartic acids and the proteins are therefore anions at neutral pH.

A protein is defined herein as acidic FGF (also referred to herein as aFGF) if it shows FGF activity in in vitro assays, binds to heparin, is an anion at neutral pH, and is immunologically reactive with antibodies prepared against human or bovine acidic FGF or against synthetic or native peptides thereof.

Acidic FGF and basic FGF are thus used herein to designate the foregoing proteins or proteins having amino acid sequences represented by those shown in FIGS. 1 and 2. Of course, these definitions are not restricted to the specific sequences shown, but include analog proteins which contain accidentally or deliberately induced alterations, such as deletions, additions, extensions, or exchanges of amino acid residues, so long as the biological activity of the FGF agonists, as measured by the foregoing in vitro assay and immunological cross-reactivity assay, is retained. Analogs of FGF with antagonist activity will, of course, have altered activity and specificity.

The various FGF analogs described herein contain deliberately induced alterations formed by directed mutagenesis techniques. These analogs retain the general secondary structure of FGF but have been mutated so as to produce various antagonist and agonist forms of FGF.

In designing such analogs, Shing et al (*Science* (1984) 223: 1269–1299) have demonstrated in vitro that basic FGF binds tightly to heparin and Maciag, T., et al, *Science* (1984) 225:932 have reported that acidic FGF also binds heparin. Thus it is likely that heparin, heparan sulfate, heparin-like glycosaminoglycans, and heparan-like glycosaminoglycans, which are present in the extracellular environment, including the extracellular matrix, may bind FGF in vivo. Since basic FGF binds in the extracellular matrix produced by vascular and capillary endothelial cells in vitro (Baird and Ling, *Biochem Biophys Res Comm* (1987) 142: 428–435), it follows that analogs of basic FGF with reduced heparin binding ability will have enhanced potency, as more FGF will reach its targeted receptor and will not be sequestered by heparin and heparin-like compounds in the extracellular environment. These analogs will be more useful therapeutically as lower dosages of the particular analog will be required per treatment.

Baird et al (*Rec Prog Horm Res* (1986) 42:143–205) have recently speculated on the regions of basic FGF, residues 26–31 and residues 115–120 illustrated in FIG. 3, which might mediate the binding to heparin. The ability of clustered basic residues, possibly in conjunction with aromatic residues, to mediate heparin binding has been described previously with respect to other proteins (Schwarzbauer et al, *Cell* (1983) 35:421–431; Cardin et al, *Biochem Biophys Res Comm* (1986) 134:783–789). Mutations created in bFGF, as described herein, replace positively charged amino acids within those targeted regions with neutral or negatively charged residues, with consideration given towards minimizing change in secondary structure of the molecule (e.g., alpha helix, beta sheet, turn motifs). In contrast to the putative heparin binding domains identified above, which do not appear to be the main functional heparin binding domains in the present studies, a third region of bFGF including residues 128–138 which contains a clustering of basic residues, was targeted as a potential heparin binding domain. Preferred mutations targeting the heparin binding domains include bFGF-K128S, bFGF-K128E, bFGF-R129T, bFGF-K134S, bFGF-K138S, and K128S/R129T. Substitutions of a basic or positively charged residue with a negatively charged residue such as glutamic acid are preferred.

An "FGF analog" is defined as a polypeptide which is the same as a native fibroblast growth factor except for one or more amino acid deletions, insertions or substitutions of the native amino acid residues in the corresponding, native fibroblast growth factor, so long as either the biological activity of or immunological cross-reactivity of the native factor is retained. An analog acts as an agonist or antagonist of the corresponding native factor.

Analogs of bFGF are designated as: bFGF-XYZ where X is the amino acid in the native human bFGF sequence that is being mutated, Y is the position of amino acid X, and Z is the amino acid residue that is being substituted for X at position Y.

Mutations of bFGF which are found to decrease or eliminate heparin binding can also be combined with other mutations found to result in the formation of analogs with either agonist or antagonist activity.

It is also within the skill of the art to create additional FGF analogs following the teaching provided herein, wherein those residues important for heparin binding are changed to other neutral amino acids (e.g., serine, alanine, glycine, etc.), or negatively charged amino acids (e.g., glutamic acid, aspartic acid), or deleted in order to reduce heparin binding activity as tested by HPLC heparin-affinity analysis as described herein. Analogs of the acidic form of FGF can be constructed as described above by deleting positively charged amino acids or by replacing positively charged amino acids within the corresponding heparin-binding domains (23–27, 115–120, 127–137) with neutral or negatively charged amino acids.

It has been found that bacterially-produced recombinant proteins can be difficult to recover in an active form. For example, it is known that cysteine-containing proteins produced in bacteria often form incorrect intramolecular cysteines which can inhibit biological function (see human interleukin-2; Wang et al, *Science* (1984) 224: 1431–1433 and human fibroblast interferon; Mark et al, *Proc Natl Acad Sci* (*USA*) (1984) 81: 5662–5666). Modifications of one or more of the cysteine residues present in the native FGF proteins may minimize incorrect disulfide bridge formation, eliminate the need for use of reducing agents to stabilize the FGF protein, and hence reduce multimerization or incorrect disulfide bonds thereby increasing the recoverable yield of the recombinantly produced analog, increasing the uniformity of the FGF preparation by maintaining it over time in a monomeric form, improving its shelf stability and reducing its half life when applied to wounds. Unexpectedly, these analogs have been shown to have augmented biological activity.

Generally, the above modifications at cysteine residues are conducted by changing a single nucleotide within the codon specifying a particular cysteine, corresponding to an amino acid substitution in the resulting protein. Cysteine residues occur in the basic form of FGF at positions 34, 78, 96, and 101, and occur in the acidic form at positions 31, 98, and 132. Since the disulfide structure of native FGF is not known, both single and multiple cysteine substitutions of FGF are exemplified herein. While these modifications produce a change in the primary structure of the protein analog, preferred analogs will generally retain the ability to effect cellular responses normally induced by FGF, unless the cysteine-substituted analogs are combined with other antagonist changes.

These same cysteine substitutions can be made in combination with other analog substitutions, such as the aforementioned heparin-binding mutants, to produce yet additional illustrative FGF analogs. Correspondingly, any of the aforementioned FGF analogs can be modified to contain one or more of the amino acid substitutions described below to produce a desired analog.

Antagonists of bFGF activity would have clinical applications in a variety of pathologies related to abnormal persistant angiogenesis (Folkman, J. and Klagsbrun, M., *Science* (1987) 235:442–447) including diabetic retinopathy, retrolental fibroplasia, neovascular glaucoma, rheumatoid arthritis, hemangiomas, angiofibromas, psoriasis, atherosclerosis and as contraceptives. In addition, it has been shown that certain solid tumors require neovascularization in order to sustain growth. Given the important role FGF plays in the process of angiogenesis, it is clear that analogs of FGF which are capable of inhibiting its effect would be useful in treating these diseases therapeutically. Thus, analogs which bind the FGF receptor yet do not elicit a biological response or that demonstrate a reduced biological response will exhibit useful antagonist properties.

The ability to elaborate a specific cell surface receptor for basic FGF has been described in a variety of cell types including baby hamster kidney cells (Neufeld and Gospodarowicz, *J Biol Chem* (1985) 260:13860–13868), bovine epithelial lens cells (Moenner, et al. *Proc Natl Acad Sci* (*USA*) (1986) 83:5024–5028), Swiss 3T3 and a murine skeletal muscle cell line (Olwin and Hauschka, *Biochemistry* (1986) 25:3487–3492) and Swiss 3T3 and aortic endothelial cells (Huang et al, *J Biol Chem* (1986) 261:11600–11607). In addition binding studies have suggested that both the basic and acidic forms of FGF can bind to the same high affinity receptor (Olwin and Hauschka, supra, and Neufeld and Gospodarowicz, *J Biol Chem* (1986) 261:5631–5637).

The interaction of a hormone (e.g., bFGF) with its receptor results in a tight, specific molecular association. This association may involve any or all of the known intermolecular attractive forces such as ion pairing or van der Waals forces. The specificity and the stability of the association are due to what may be thought of as "exactness of fit" (the precise three-dimensional molecular conformations of the two proteins, receptor and hormone) and "tightness of fit" (the fact that these molecular structures are composed of precise amino acid sequences which therefore results in specific intermolecular attractions due to energetically favorable juxtaposition of amino acid side chains). Thus, amino acid substitutions, deletions and insertions within receptor binding regions may effect either molecular conformation of the region or amino acid side chain interactions (between hormone and receptor) or both. Changes which stabilize favorable conformation or enhance amino acid side chain interactions will result in increased receptor affinity while those which destabilize favorable conformation or decrease amino acid side chain interactions will result in decreased receptor affinity. The former changes are useful in themselves as their introduction into agonists may result in more potent agonists and their introduction into antagonists may result in more potent antagonists. The latter changes are useful in terms of defining amino acid segments crucial to receptor binding.

Schubert et al (*J Cell Biol* (1987) 104:635–643) have shown that synthetic peptides containing fragments of bFGF (residues 33–77 and 112–129 numbered according to FIG. 3) inhibit binding of bFGF to its receptor. Therefore, these regions appear to contain FGF receptor binding sequences. We have introduced amino acid substitutions into human basic FGF within these putative receptor binding regions and additional regions adjacent to the latter (e.g., amino acids 99–111 which exhibit strong homology to the equivalent amino acid sequence region in acidic FGF). Both charged (positive and negative) and aromatic amino acids were targeted for replacement with neutral residues. These substitutions were made with consideration given towards minimizing changes in the secondary structure of the resultant protein. Accordingly, the analogs D99A and R116T appear to exhibit increased receptor affinity and 3T3 mitogenic activity, respectively, whereas analogs E105S and Y112A exhibit decreased receptor binding (see Table 3 herein).

For purposes of the present invention the following terms are defined below.

"Agonist" refers to an FGF analog capable of combining with the FGF receptor and producing a typical biological response. For example, an FGF agonist might be a protein than can bind to the FGF receptor but has reduced ability to bind heparin, thereby creating a more potent therapeutic.

"Antagonist" refers to an FGF analog that opposes the effects of FGF by a competitive mechanism for the same receptor sites. The antagonist has reduced ability to induce secondary biological responses normally associated with FGF.

"Site-specific mutagenesis" or "directed mutagenesis" refers to the use of the oligonucleotide-directed mutagenesis procedure, which entails using a synthetic oligonucleotide primer that is complementary to the region of the bFGF gene at the specific codon or codons to be altered, but which contains single or multiple base changes in that codon. By this technique, a designer gene may be produced that results in a specific amino acid being replaced with any other amino acid of choice. When deletion is desired the oligonucleotide primer lacks the specific codon. Conversion of, for example, a specific cysteine, to neutral amino acids such as glycine, valine, alanine, leucine, isoleucine, tyrosine, phenylalanine, histidine, tryptophan, serine, threonine or methionine is a preferred approach. Serine and alanine are the most preferred replacements because of their chemical analogy to cysteine. When a cysteine is deleted, the mature analog is one amino acid shorter than the native parent protein or the microbially produced wild type bFGF.

"Purified" or "pure" refers to material which is free from substances which normally accompany it as found in its native state. Thus "pure" acidic human FGF (hFGF), for example, refers to acidic hFGF which does not contain materials normally associated with its in situ environment in human brain or pituitary. Of course, "pure" acidic hFGF may include materials in covalent association with it, such as glycoside residues.

"Operably linked" refers to a juxtaposition wherein the components are configured so as to perform their usual function. Thus, control sequences or promoters operably linked to a coding sequence are capable of effecting the expression of the coding sequence.

"Control sequence" refers to a DNA sequence or sequences which are capable, when properly ligated to a desired coding sequence, of affecting its expression in hosts compatible with such sequences. Such control sequences include at least promoters in both procaryotic and eucaryotic hosts, and optionally, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the desired characteristics conferred on the originally transformed cell. In the present case, for example, such a characteristic might be the ability to produce recombinant FGF analogs.

B. General Description

Utility and Administration

The invention provides DNAs encoding growth factor protein analogs which have two diverse applications. The first application is similar to FGF in that the analogs augment tissue repair by encouraging vascularization and/or cell growth or cell survival. These purified growth factors are generally applied topically to the traumatized or diseased tissue in order to stimulate vascularization, regeneration, and healing. Appropriate substrates are burns, wounds, bone fractures, surgical abrasions such as those of plastic surgery, or others requiring repair. Because application of these factors accelerates healing, they also reduce the risk of infection.

Indications wherein FGF is of value in encouraging neovascularization include musculo-skeletal conditions such as bone fractures, ligament and tendon repair, tendonitis, and bursitis; skin conditions such as burns, cuts, lacerations, bed sores, and slow-healing ulcers such as those seen in diabetics; and in tissue repair during ischaemia and myocardial infarction.

In addition to analogs which augment wound healing, analogs of FGF can be constructed which inhibit angiogenesis. Analogs of FGF which can antagonize the FGF angiogenesis activity would be clinically useful for treating certain diseases where neovascularization is the dominant pathology, such as retinopathies of the eye including diabetic retinopathy and neovascular glaucoma; skin disorders including psoriasis and retrolental fibroplasia; chronic inflammation; rheumatoid arthritis; atherosclerosis; and certain neoplasms that are highly angiogenic, such as the growth of certain benign and alignant tumors such as hemangiomas and angiofibromas, and solid tumors.

Formulations of the recombinantly produced growth factors using available excipients and carriers are prepared according to standard methods known to those in the art. The proteins can be formulated as eyedrops, lotions, gels, powder, dressing, as part of a controlled release system, or ointments with additional active ingredients, such as antibiotics, if desired.

For topical administration, which is the most appropriate with regard to superficial lesions, standard topical formulations are employed using, for example, 10 ng/ml–100 mg/ml solutions; the preferred range is 10 ug/ml–10 mg/ml. Such solutions would be applied up to 6 times a day to the affected area. In certain applications, such as burns, a single dose would be preferred. In other applications, such as ulcers, multiple doses may be preferred. The concentration of the ointment or other formulation depends, of course, on the severity of the wound or stage of disease and the nature of the subject. In most protocols, the dose is lowered with time to lessen likelihood of scarring. For example, the most severe wounds, such as third degree burns, are typically treated with a 100 ug/ml composition, but as healing begins, the dose is progressively dropped to approximately 10 ug/ml or lower, as the wound heals. A topical formulation for EGF using BSA as carrier was disclosed by Franklin, J. D., et al, *Plastic and Reconstruc Surg* (1979) 64:766–770.

For treatment of pathologies related to persistent angiogenesis wherein FGF inhibitors are to be applied, the concentration of the formulation is generally 10-fold higher, regardless of the mode of administration. The higher dosage assures that the FGF inhibitor is able to compete effectively with endogenously produced FGF. Thus for topical administration of the FGF inhibitor used to treat psoriasis and retrolental fibroplasia, the dosage would be increased 10-fold.

For arthritis and bone and tissue repair, administration is preferred locally by means of subcutaneous implant, staples or slow release formulation implanted directly proximal the target. Surgery may be required for such conditions as bone injuries, thus making implantation directly practical. Slow-release forms can be formulated in polymers, such as Hydron (Langer, R., et al, *Nature* (1976) 263:797–799) or Elvax 40P (Dupont) (Murray, J. B., et al, *In Vitro* (1983) 19:743–747). Other sustained-release systems have been suggested by Hsieh, D. S. T., et al, *J Pharm Sci* (1983) 72:17–22), and a formulation specifically for epidermal growth factor, but not preferred in the present invention, is suggested by Buckley, A., *Proc Natl Acad Sci (USA)* (1985) 82:7340–7344.

As with topical administration, for sustained release delivery, the concentration of FGF in the formulation depends on a number of factors, including the severity of the condition, the stability of FGF at 37° C., the rate of FGF release from the polymer, and the agonist or antagonist nature of the FGF analog. In general, the formulations are constructed so as to achieve a constant local concentration of about 100 times the serum level of factor or 10 times the tissue concentration, as described by Buckley et al (*Proc Natl Acad Sci (USA)* (supra)). Based on an FGF concentration in tissue of 5–50 ng/g wet weight (comparable to EGF at 60 ng/g wet weight), release of 50–5000 ng FGF per hour is acceptable. The initial concentration, of course, depends on the severity of the wound or advancement of pathology.

For treatment in diseases common to ophthalmology, such as retinopathies and neovascular glaucoma, eyedrop formulation or direct injection into the eye would be two preferred routes of administration. Liquid formulations for these applications are generally known in the art and include formulation in buffer or physiological saline, or other appropriate excipient. Dosage levels may be supplied between 1 ug/ml and 10 mg/ml from two to four times a day.

It is expected that FGF may act in concert, and even synergistically, with other growth factors such as epidermal growth factor (EGF), the transforming growth factors (TGF-alpha or TGF-), insulin-like growth factors (IGF-1 and IGF-2), and/or platelet-derived growth factor (PDGF). In addition, specifically for bone repair, it may act in synergy with agonists or antagonists of parathyroid hormone or calcitonin, since these compounds promote bone growth and resorption. Therefore, also included within the compositions and administration protocols of the invention are embodiments wherein the FGF of the invention is administered in the same composition with, or in the same protocol with, one or more of the foregoing factors, thus more effectively to achieve the desired tissue repair.

Since FGF is effective in promoting neurite outgrowth, nerve regeneration, and neuronal survival, it may be useful for treatment of certain neurological disorders such as Alzheimer's and Parkinson's diseases, amyotrophic lateral sclerosis, stroke, peripheral neuropathies, and general aging of the nervous system, as well as traumatic injury to the spinal cord and peripheral nerves. Administration of the drug for these indications is preferably by implant in formulations similar to those set forth above in connection with rheumatoid arthritis and bone healing. The drug may also be delivered by means of implants of cell cultures by means of implants of cell cultures which produce FGF. Treatment of neurological disorders may also involve transplantation of new cells or tissues to functionally replace damaged neural tissue (e.g., adrenal and fetal brain tissue transplants in Parkinsonian patients). In such cases, the degree of success of transplantation as well as the degree of function of the transplanted tissue are enhanced by treating the cell cultures or tissue explants with the FGF or analog preparations of the invention prior to transplantation and/or by administration of FGF or FGF analogs of the invention following transplantation.

FGF and analogs thereof may also be injected directly into the spinal fluid or into the brain by means of canulation or by administration using osmotic minipumps or they may be applied systemically. For atherosclerosis peripheral neuropathies and the like, and tumor angiogenesis, systemic administration is preferred, with administration of the drug delivered initially at the time of surgery, where appropriate.

Systemic formulations are generally as are known in the art and include formulation in buffer or physiological saline, or other appropriate excipient. Dosage levels for FGF agonist administration are approximately those of wound healing; however, for tissue culture, explant maintenance, atherosclerosis or tumor angiogenesis, it may be supplied at 1.0–100 ng/ml of serum or culture medium.

In addition, it has been shown that angiogenic stimuli, such as those provided by the FGF proteins discussed herein, result in the release of plasminogen activator (PA) and of collagenase in vitro (Gross, J. L., et al, *Proc Natl Acad Sci (USA)* (1983) 80:2623–2627). Therefore, the FGF proteins of the invention are also useful in treatment of conditions which respond to these enzymes. While it may be necessary in acute situations (such as the presence of a blood clot associated with stroke or heart attack) directly to administer large doses of PA to dissolve the clot, for treatment of chronic propensity to form embolisms, administration of FGF to maintain a suitable level of PA in the blood stream may be desirable. Therefore, for this indication, systemic administration of the drug, especially an analog with reduced heparin-binding ability, using conventional means such as intramuscular or intravenous injection, is preferred.

The invention provides practical quantities of pure FGF analogs for use in connection with the foregoing indications. Specific growth factors are exemplified herein, each of which is apparently active in at least three forms. Both acidic and basic analogs are considered to occur in long, primary, and short forms, as described above. It is considered that the N-terminal methionine of the long forms is processed off when the protein is produced in eucaryotic systems, and that the subsequent amino acid residue is derivatized, probably by acetylation, post-translation.

While FGF in its various forms does not have a recognized signal sequence, it must somehow be secreted or retrieved from the cell, since it acts outside the cells producing it at a membrane-bound receptor. Therefore, while it may not be secreted by the recognized constitutive secretion pathway, its secretion is accomplished by some means, for example by cell lysis or by exocytosis, by association with a glycosaminoglycan, such as heparan sulfate or heparin. For most tissues from which FGF is naturally derived, and for many mammalian expression systems, such release may be achieved by securing exocytosis with a calcium ionophore, such as the commonly employed A23187 (CalBiochem), which, in in vitro conditions, is added to the culture medium at 1–10 uM in the presence of 1 mM $CaCl_2$. For expression systems derived from macrophages or monocytes, other activation methods have been shown to be effective, such as the addition of lipopolysaccharide (LPS) at 10 ug/ml or the addition of *E. coli* endotoxin (Difco) (300 ng/ml). These stimulators have been shown to release the analogous factor interleukin-1 from macrophages by March, C. J., et al, *Nature* (1985) 315:641–647. These techniques can also be employed in releasing recombinantly produced FGF proteins when produced intracellularly without added signal sequences, as described below. Additional stimulators for release of intracellularly produced proteins include the phorbol esters and the triglycerides.

Gene Retrieval

The general strategy whereby the illustrated FGF-encoding sequences were obtained is as described in co-pending U.S. Ser. No. 869,382, filed May 30, 1986, Abraham, J. A. et al, *EMBO J* (1986) supra, and Abraham, J. A. et al, *Science* (1986) 233:545–548, all of which are incorporated herein by reference.

Expression of FGF Genes

The DNA sequences described herein can be expressed in appropriate expression systems. Of course, for the DNAs disclosed herein, the foregoing protocol for retrieving the genomic or cDNA FGF sequences need not be repeated, but conventional chemical synthesis methods can suitably be employed. Alternatively, the gene encoding basic FGF can be retrieved from the deposited bacteriophage lambdaBB2 and converted to the human form. Site-directed mutagenesis permits adjustment of the DNA to obtain any desired form of the protein. DNA sequences can be provided with appropriate controls suitable for any host, including bacteria, yeast, or eucaryotic cells. Exemplary control sequence DNAs and hosts are given in paragraph C.1 below.

In particular, complete DNA encoding any of the FGF analogs described herein can be constructed, for example, using a combination of recombinant and synthetic methods to obtain each of the DNA analog sequences of FGF. These gene sequences have been constructed with convenient restriction sites bounding the FGF coding sequence so that the entire gene may be inserted on an ~503 bp NcoI-HindIII restriction fragment for insertion into an appropriately digested host vector such that the FGF coding sequence is operably linked to control sequences present on the vector. Intracellularly produced forms of the FGF protein analogs can be obtained by cell lysis, or their release from the cells can be stimulated by using heterologous signal sequences fused to the gene sequence using the known relationship of the signal sequence to cleavage site to obtain the protein in the desired form. Particularly preferred are bacterial expression systems which utilize control systems compatible with *E. coli* cells, such as plasmids pUC9-TSF11 and pUC9delH3-pTSF-3. These vectors are derived from pUC9 (Messing and Vieira, *Gene* (1982) 19:259–268), which contains parts of pBR322 and M13mp9 and a multiple cloning site polylinker.

The recombinant FGF proteins thus produced are then purified in a manner similar to that utilized for purification of FGF from natural sources, but purification is considerably simpler, as the proteins form a much larger proportion of the starting material.

B. Standard Methods

Most of the techniques which are used to transform cells, construct vectors, construct oligonucleotides, perform site-specific mutagenesis, and the like are widely practiced in the art, and most practitioners are familiar with the standard resource materials which describe specific conditions and procedures. However, for convenience, the following paragraphs may serve as a guideline.

B.1. Hosts and Control Sequences

Both procaryotic and eucaryotic systems may be used to express the FGF analog encoding sequences; procaryotic hosts are, of course, the most convenient for cloning procedures. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the -lactamase (penicillinase) and lactose (lac) promoter systems (Chang, et al, *Nature* (1977) 198:1056), the tryptophan (trp) promoter system (Goeddel, et al, *Nucleic Acids Res* (1980) 8:4057), the lambda-derived $P_L$ promoter (Shimatake, et al, *Nature* (1981) 292:128) and N-gene ribosome binding site, and the trp-lac (trc) promoter system (Amann and Brosius, *Gene* (1985) 40:183).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2 u origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enz* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO, HeLa baby hamster kidney (BHK), CV-1, COS, MDCK, NIH 3T3, L, and Chinese hamster ovary (CHO) cells. Expression vectors for such cells ordinarily include promoters and control sequences compatible with mammalian cells such as, for example, the commonly used early and late promoters from Simian Virus 40 (SV40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

B.2. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the $RbCl_2$ method described in Maniatis, et al, *Molecular Cloning: A Laboratory Manual* (1982) Cold Spring Harbor Press, p. 254 and Hanahan, D., *J Mol Biol* (1983) 166:557–580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D., *Nature* (1978) 275:104–109 or of Hinnen, A., et al, *Proc Natl Acad Sci (USA)* (1978)

B.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth in ||C.1 above. For the pertinent coding sequence, initial construction may be, and usually is, a matter of retrieving the appropriate sequences from CDNA libraries, genomic DNA libraries, or deposited plasmids. However, once the sequence is disclosed it is possible to synthesize the entire gene sequence in vitro starting from the individual nucleoside derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles [lambda-$^{32}$P]-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20 to 25° C. in 50 mM Tris pH 7.6, 50 mM NaCl, 6 mM $MgCl_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 ul volumes under the following standard conditions and temperatures: for example, 20 mM Tris-Cl pH 7.5, 10 mM $MgCl_2$, 10 mM DTT, 33 ug/ml BSA, 10 mM-50 mM NaCl, and either 40 uM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 ug/ml total DNA concentrations (5–100 nM total end concentration). Intermolecular blunt end ligations are performed at 1 uM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per ug of vector at 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from CDNA or genomic DNA which require sequence modifications, site specific mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide primer complementary to a single stranded phage DNA to be mutagenized except for limited mismatching, representing the desired mutation.

The size of the oligonucleotide primer is determined by the requirement for stable hybridization of the primer to the region of the gene in which the mutation is to be induced, and by the limitations of the currently available methods for synthesizing oligonucleotides. The factors to be considered in designing oligonucleotides for use in oligonucleotide-directed mutagenesis (e.g., overall size, size of portions flanking the mutation site) are described by Smith, M. and Gillam, S. in *Genetic Engineering: Principles and Methods*, Plenum Press (1981) 3:1–32. In general the overall length of the oligonucleotide will be such as to optimize stable, unique hybridization at the mutation site with the 5' and 3' extensions from the mutation site being of sufficient size to avoid editing of the mutation by the exonuclease activity of the DNA polymerase. Oligonucleotides used for mutagenesis in accordance with the present invention usually contain from about 18 to about 45 bases, preferably from about 23 to about 27 bases. They will usually contain at least about three bases 3' of the altered or missing codon.

The method for preparing the modified bFGF genes generally involves inducing a site-specific mutagenesis in the bFGF gene at a specific codon using a synthetic nucleotide primer which omits the codon or alters it so that it codes for another amino acid. It must be recognized that when deletions are introduced, the proper reading frame for the DNA sequence must be maintained for expression of the desired protein.

The primer is hybridized to single-stranded phage such as M13, fd, or deltaX174 into which a strand of the bFGF gene has been cloned. It will be appreciated that the phage may carry either the sense strand or antisense strand of the gene. When the phage carries the antisense strand the primer is identical to the region of the sense strand that contains the codon to be mutated except for a mismatch with that codon that defines a deletion of the codon or a triplet that codes for another amino acid. When the phage carries the sense strand the primer is complementary to the region of the sense strand that contains the codon to be mutated except for an appropriate mismatch in the triplet that is paired with the codon to be deleted. Conditions that may be used in the hybridization are described by Smith, M. and Gillam, S., supra. The temperature will usually range between about 0° C. and 70° C., more usually about 10° C. to 50° C. After the hybridization, the primer is extended on the phage DNA by reaction with DNA polymerase I, $T_4$ DNA polymerase, reverse transcriptase, or other suitable DNA polymerase. The resulting dsDNA is converted to closed circular dsDNA by treatment with a DNA ligase such as $T_4$ DNA ligase. DNA molecules containing single-stranded regions may be destroyed by S1 endonuclease treatment.

The resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

C.4. Verification of Construction

In the constructions set forth below, correct ligations for plasmid construction are confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem* (1981) 114:193–197 and Birnboim, H. C., et al, *Nucleic Acids Res* (1979) 7:1513–1523. The isolated DNA is analyzed by dot blot analysis as described by Kafatos, F. C., et al, *Nucl Acid Res* (1977) 7:1541–1552, restriction enzyme analysis, or sequenced by the dideoxy nucleotide method of Sanger, F., et al, *Proc Natl Acad Sci (USA)* (1977) 74:5463, as further described by Messing, et al, *Nucleic Acids Res* (1981) 9:309, or by the method of Maxam, et al, *Methods in Enzymology* (1980) 65:499.

C.5. Hosts Exemplified

Host strains used in cloning and procaryotic expression herein are as follows:

For cloning and sequencing, and for expression of construction under control of most bacterial promoters, *E. coli* strains such as MC1061, DH1, RR1, B, C600hfl, K803, HB101, JA221, and JM101 were used.

D. Illustrative Procedure

The following examples are intended to illustrate but not to limit the invention. The DNA encoding the FGF starting material was obtained initially by screening a bovine genomic library and obtaining a pivotal probe, followed by retrieval of additional DNA. However, it would not be necessary to repeat this procedure, as the sequence of the pivotal probe is now known and could thus be constructed chemically in vitro. In addition, bacteriophage harboring bovine aFGF and bFGF and human aFGF and bFGF sequences are deposited at the American Type Culture Collection. Thus, the DNA sequence used as the starting material for the mutagenesis in the following examples is available from a variety of sources.

EXAMPLE 1

Construction of pTrp-233 Bacterial Expression Plasmid

1. Construction of the Synthetic Tryptophan Operon Promoter and Operator Regulatory Sequence The ten oligodeoxynucleotides shown in FIG. 4 were synthesized by the phosphotriester method and purified. 500 pmole of each oligodeoxynucleotide except 1 and 10 were phosphorylated individually in 20 ul containing 60 mM Tris-HCl, pH 8, 15 mM DTT, 10 mM MgCl$_2$, 20 uCi of [lambda-$^{32}$p]-ATP and 20 units of polynucleotide kinase (P/L Biochemicals) for 30 min. at 37° C. This was followed by the addition of 10 ul containing 60 mM Tris-HCl, pH 8, 15 mM DTT, 10 mM MgCl$_2$, 1.5 mM ATP and 20 additional units of polynucleotide kinase followed by another 30 min incubation at 37° C. Following incubation the samples were incubated at 100° C. for 5 min. 500 pmole of oligodeoxynucleotides 1 and 10 were diluted to 30 ul in the above buffer without ATP.

16.7 pmole of each oligodeoxynucleotide constituting a double stranded pair (e.g. oligodeoxynucleotides 1 and 2, 3 and 4 etc. FIG. 4) were mixed and incubated at 90° C. for 2 min followed by slow cooling to room temperature. Each pair was then combined with the others in the construction and extracted with phenol/chloroform followed by ethanol precipitation. The oligodeoxynucleotide pairs were reconstituted in 30 ul containing 5 mM Tris-HCl, pH 8, 10 mM MgCl$_2$, 20 mM DTT, heated to 50° C. for 10 min and allowed to cool to room temperature followed by the addition of ATP to a final concentration of 0.5 mM. 800 units of T$_4$ DNA ligase were then added and the mixture incubated at 12.5° C. for 12–16 hours.

The ligation mixture was extracted with phenol/chloroform and the DNA ethanol precipitated. The dried DNA was reconstituted in 30 ul and digested with EcoRI and PstI for 1 hour at 37° C. The mixture was extracted with phenol/chloroform and ethanol precipitated followed by separation of the various double stranded DNA segments by electrophoresis on an 8% polyacrylamide gel, according to the method of Laemmli et al, *Nature* (1970) 227:680. The DNA fragments were visualized by wet gel autoradiography and a band corresponding to approximately 100 bp in length was cut out and eluted overnight as described. The excised synthetic DNA fragment was ligated to plasmids M13-mp8 or M13-mp9 (Messing and Vieira, supra) similarly digested with EcoRI and PstI, and submitted to dideoxynucleotide sequence analysis (Sanger et al. supra) to confirm the designed sequence shown in FIG. 4. This designed sequence contains the promoter (−35 and −10 regions) and operator regions of the tryptophan operon (trp) as well as the ribosome binding region of the tryptophan operon leader peptide. Analogous sequences to that shown in FIG. 4 have been proven to be useful in the expression of heterologous proteins in *E. coli* (Hallewell, R. A., and Emtage, S., *Gene* (1980) 9:27–47, Ikehara, M., et al. *Proc Natl Acad Sci (USA)* (1984) 81:5956–5960).

2. Construction of the Synthetic trp Promoter/Operator Containing Plasmid, pTrp-233

Plasmid pKK233-2 (Amann, E. and Brosius, J., supra) was digested to completion with NdeI followed by the filling in of the termini by the method of Maniatis et al, *Molecular Cloning*, Cold Spring Harbor Laboratories, 1982 at p. 394, with 5 units of *E. coli* polymerase I, Klenow fragment (Boehringer-Mannheim, Inc.) and the addition of dATP, dCTP, dGTP and TTP to 50 uM. This was incubated at 25° C. for 20 min. Following phenol/chloroform extraction and ethanol precipitation, the NdeI-digested DNA was ligated and transformed into *E. coli* (Nakamura, K. et al, *J Mol Appl Genet* (1982) 1: 289–299). The resulting plasmid lacking the NdeI site was designated pKK-233-2-Nde.

Twenty nanograms of plasmid pKK-233-2-Nde was digested to completion with EcoRI and PstI followed by calf intestinal phosphatase treatment (Boehringer Manheim) in accordance with Maniatis et al., supra at pp. 133–134. Fifty nanograms of the synthetic trp promoter/operator sequence obtained from M13 RF, (described above) by digesting with EcoRI and PstI, were mixed with ten nanograms of EcoRI-PstI digested pKK-233-2-Nde and ligated with T$_4$-DNA-ligase as described followed by transformation into *E. coli* JA221 1pp$^-$/I'lacI. Transformants were screened for the presence of plasmid DNA containing the 100 bp EcoRI-PstI synthetic trp promoter/operator; the correct plasmid was then isolated and designated pTrp-233.

EXAMPLE 2

Construction of Plasmid pTSF11

A. Human Basic Fibroblast Growth Factor

The bovine basic FGF cDNA was used to develop hybridization probes to isolate basic FGF clones from human cDNA and genomic libraries as described in U.S. Ser. No. 869,382, supra, Abraham, J. A. et al, *Science* (1986) supra, and Abraham, J. A. et al, *The EMBO Journal* (1986) supra, all of which are incorporated herein by reference.

There are only two amino acid differences between basic bovine FGF and human FGF, at position 123, where the bovine protein has Ser and the human protein has Thr, and at position 137, where the bovine protein has Pro and the human has Ser. These differences are the result of a single nucleotide difference in each case; therefore bovine CDNA may conveniently be modified by site directed mutagenesis as described below to encode the human protein, and, indeed, standard site-specific mutagenesis techniques were used to alter these codons. The lambda BB2 clone (ATCC No. 40196) was digested with EcoRI and the 1.4 kb region spanning the bFGF protein-encoding portion was ligated into the EcoRI site of M13mp8 and phage carrying the insert in the correct orientation were recovered. The in vitro mutagenesis was carried out in the presence of three oligonucleotides: the "universal" primer, a 17-mer; the mutagenic 16-mer 5'-GAAATACACCAGTTGG-3' (SEQ ID NO: 7); which alters the coding sequence at codon 123, and the mutagenic 17-mer 5'-ACTTGGATCCAAAACAG-3 (SEQ ID NO: 8), which alters the sequence at codon 137. The mutagenized phage was also subjected to a second round of in vitro primer-directed mutagenesis to create a HindIII site 34 bp downstream from the translation termination codon using the mutagenic 25-mer, 5'-TTTTACATGAAGCTTTATATTTCAG-3' (SEQ ID NO: 9). The resultant mutated DNA was sequenced by dideoxynucleotide sequence analysis (Sanger et al, supra) to confirm that the desired mutagenesis had occurred, and the approximately 630 bp fragment spanning the FGF coding region was excised with HindIII and ligated into HindIII digested pUC13 to obtain the intermediate plasmid pJJ15-1.

B. Construction of Gene with Synthetic Coding Region for N-terminal End of FGF Gene In order to lower the G+C content of the 5' end (the first 125 base pairs) of the coding region contained in pJJ15-1, a synthetic DNA fragment was constructed with the sequence shown below using the following synthetic oligonucleotides. The oligonucleotides were annealed in pairs, ligated together sequentially, and ligated into HindIII cut m13mp9. The sequence of the synthetic 125 bp insert in mp9 was confirmed by dideoxy sequencing. The NdeI to HhaI subfragment of the synthetic insert was isolated, joined to the 377 base pair, HhaI-to-HindIII DNA fragment from JJ15-1 that spans approximately the carboxy-terminal three quarters of the basic FGF coding sequence, and then ligated into the NdeI and HindIII sites of the expression vector pTrp-233 to yield the plasmid pTFS11.

Oligonucleotides

| Number | Sequence | |
|---|---|---|
| 1670 | 5'-pAGCTTCATATGGCTGCTGGTTCTATCACTACC | (SEQ ID NO:10) |
| 1623R | 5'-pCTGCCAGCTCTGCCAGAAGACGGTGGTT | (SEQ ID NO:11) |
| 1624R | 5'-pCTGGTGCCTTCCCACCAGGTCACTTCAA | (SEQ ID NO:12) |
| 1625R | 5'-pAGACCCAAAACGTCTGTACTGCAAAAAC | (SEQ ID NO:13) |
| 1680 | 5'-pGGTGGTTTCTTCCTGCGCA | (SEQ ID NO:14) |
| 1679 | 5'-pTAGAACCAGCAGCCATATGA | (SEQ ID NO:15) |
| 1622 | 5'-pTCTTCTGGCAGAGCTGGCAGGGTGA | (SEQ ID NO:16) |
| 1619 | 5'-pACCTGGTGGGAAGGCACCAGAACCACCG | (SEQ ID NO:17) |
| 1626 | 5'-pAGTACAGACGTTTTGGGTCTTTGAAGTG | (SEQ ID NO:18) |
| 1673 | 5'-pAGCTTGCGCAGGAAGAAACCACCGTTTTTGC | (SEQ ID NO: 19) |

Construction of Synthetic Gene for the Amino Terminal Region of bFGF

HindIII NdeI (SEQ ID NOS: 20–21)

```
        10         20         30         40
AGCTTCATATG GCTGCTGGTT CTATCACTAC CCTGCCAGCT
    AGTATAC CGACGACCAA GATAGTGATG GGACGGTCGA 50         60         70         80
CTGCCAGAAG ACGGTGGTTC TGGTGCCTTC CCACCAGGTC
GACGGTCTTC TGCCACCAAG ACCACGGAAG GGTGGTCCAG 90        100        110        120
ACTTCAAAGA CCCAAAACGT CTGTACTGCA AAAACGGTGG
TGAAGTTTCT GGGTTTTGCA GACATGACGT TTTTGCCACC

HhaI
       130
TTTCTTCCTG CGCA
AAAGAAGGAC GCGTTCGA
```

Figure 5:
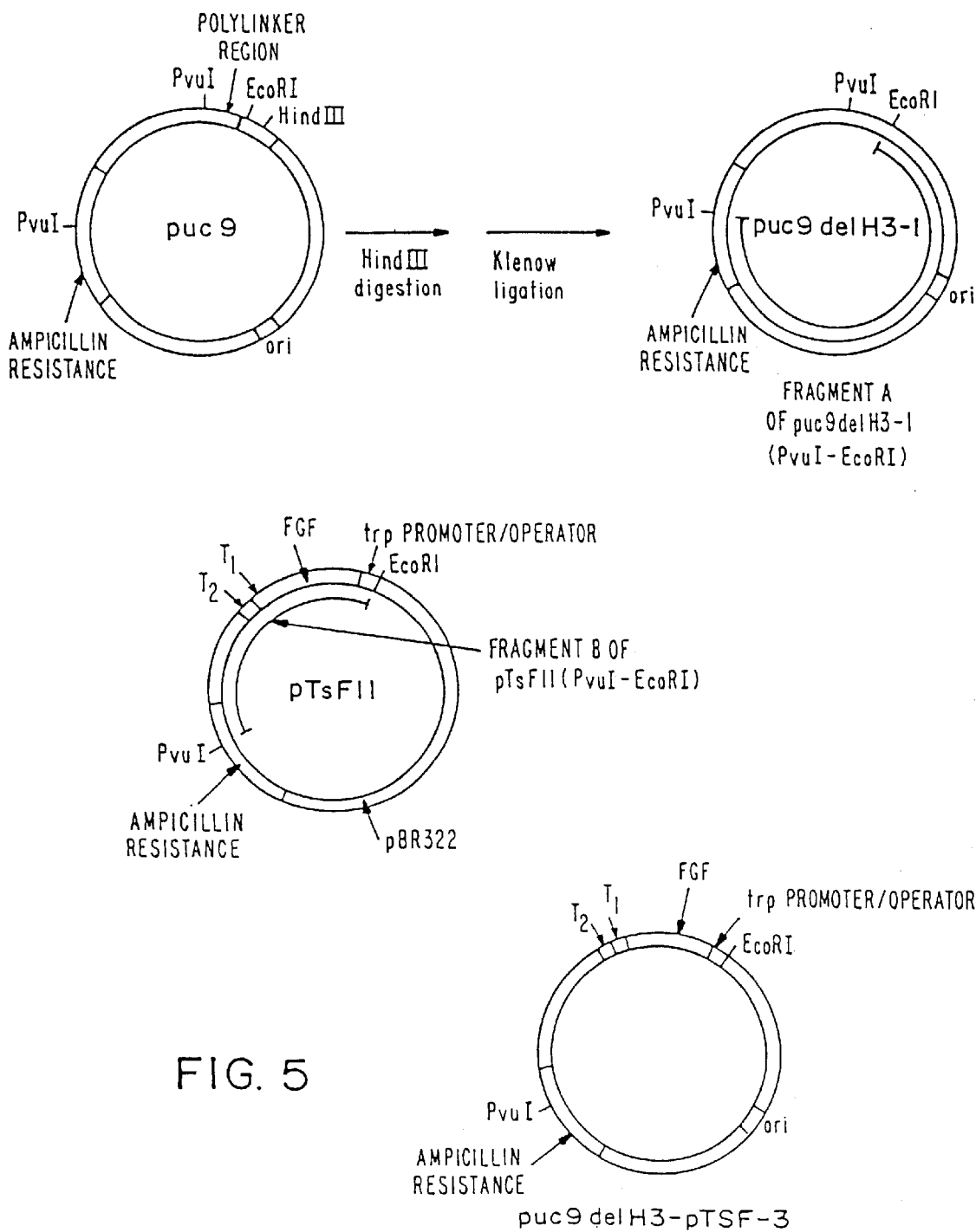
FIG. 5 is a flow chart of the construction of plasmid pUC9delH3-pTSF-3.

A plasmid map of pTSF11 is given in FIG. 5 of the accompanying drawings.

EXAMPLE 3

Preparation of Expression Vector for Mutagenized Gene Inserts

The HindIII site of the polylinker region of plasmid pUC9 was removed so as to facilitate subcloning mutated DNA into the final expression vector illustrated in FIG. 5. Approximately 5 ug of pUC9 (New England Biolabs) was digested with HindIII (20 units; New England Biolabs) according to the manufacturers instructions in 0.05 ml. The reaction was then supplemented with 0.5 mM dNTPs and the Klenow fragment of DNA Polymerase I (5 units; Boehringer Manheim) and incubated for 30 minutes at 15° C. The reaction was then extracted twice with an equal volume of phenol/chloroform (1/1), twice with chloroform, made 0.2M. NaCl, and then precipitated with two and a half volumes of ethanol. The precipitate was collected by centrifugation (15,000 g in a Microfuge at 4° C.), lyophilized, and then incubated in 0.1 ml with 1×kinase ligase buffer, 1 mM ATP, and $T_4$ DNA ligase (20 units; New England Biolabs) for 4 hours at 12° C.

An aliquot of the reaction (0.01 ml) was then used to transfect competent MC1061 cells. The transfected bacteria were grown overnight on L agar plates supplemented with 100 ug/ml ampicillin. DNA was isolated from 6 colonies by the alkaline lysis procedure and tested for the loss of the HindIII site. A bacteria containing the plasmid, pUC9delH3-1, was isolated. The plasmid DNA was prepared and 10 ug was digested in 0.4 ml with PvuI (20 units; New England Biolabs) and EcoRI (50 units; New England Biolabs) for 2 hours according to the manufacturers instructions. The reaction was then extracted twice with an equal volume of phenol/chloroform (1/1) and twice with an equal volume of phenol and then precipitated with isopropanol. The precipitate was collected by centrifugation, washed with 70% ethanol, lyophilized, resuspended in 0.008 ml water and the ~2.07 kb PvuI-EcoRI fragment of pUC9delH3-1 (designated fragment A) containing the origin of replication was isolated by acrylamide gel electrophoresis.

Concurrently pTSF11 DNA (10 ug) was incubated with PvuI (10 units) and EcoRI (10 units) in 0.15 ml for 1 hour at 37° C. according to the manufacturers directions and collected as described above. The ~1.3 kb PvuI-EcoRI fragment of pTSF11 containing the Trp promoter/operator region, FGF coding region and the transcription termination sequences, designated fragment B of pTSF11, was isolated by polyacrylamide gel electrophoresis and ligated to the ~2.07 kb PvuI-EcoRI fragment A of pUC9delH3-1, and used to transfect competent E. coli HB101 cells. The bacteria were grown overnight on L agar plates supplemented with 100 ug/ml ampicillin. Plasmid DNA from one recombinant, pUC9delH3-pTSF-3, was isolated and shown to contain the expected restriction map (HindIII cuts the plasmid only once; the sizes of HindIII-EcoRI, HindIII-PvuI and HindIII-PstI fragments are approximately 560 and 2900, 800 and 2700, and 560 and 2900 bp respectively. DNA from the plasmid pUC9delH3-pTSF-3 was isolated and 200 ug incubated in 1.0 ml with 100 units of HindIII, 100 units of EcoRI, 5 mM spermidine for 4 hours at 37 ° C. according to the manufacturers instructions. The reaction was butanol extracted to reduce the volume to 0.7 ml and then extracted with phenol/chloroform and chloroform as described above. The DNA was collected by ethanol precipitation and the ~2.9 kb HindIII-EcoRI fragment containing the ampicillin resistance gene, the origin of replication and the two transcription stop signals, designated fragment C of pUC9delH3-pTSF-3, was isolated by two sequential runs on polyacrylamide gels. This vector fragment serves as the preferred vector for expressing any of the DNA which has been altered by in vitro mutagenesis. The construction of this vector is illustrated in FIG. 5.

Plasmid pUC9-pTSF11, a vector closely resembling plasmid pUC9delH3-pTSF-3 but containing an intact HindIII site in the multiple site polylinker region, can also be used as a preferred vector for expressing both recombinantly produced FGF (all forms) and any of the analogs of the present invention. This vector was constructed by individually digesting plasmids pUC9 and pTSF11 with PvuI and EcoRI, isolating the ~2.07 kb PvuI-EcoRI vector fragment from pUC9 and the ~1.3 kb PvuI-EcoRI fragment containing the trp promoter/operator region, FGF coding region, and the transcription termination sequences from pTSF11, and ligating the two isolated fragments. This vector can then be used to express the FGF analog gene sequences as taught with pUC9-pTSF11 by inserting the HindIII-EcoRI DNA cassettes into the appropriately digested vector and transforming E. coli bacterium.

EXAMPLE 4

Generalized Procedure for Production of FGF Mutants

The following protocol can be used to construct all of the DNA sequences encoding the FGF analogs described herein. Plasmid FGFt7910 was constructed by ligating the ~603 bp EcoRI-HindIII DNA fragment of pTSF11 (comprising the Trp promoter region and the DNA encoding human bFGF) into the EcoRI-HindIII sites of an M13mp9 vector. Once the single-stranded DNA of FGFt7910 was isolated, in vitro mutagenesis, as described by Zoller and Smith, supra, may be performed utilizing one or more of the synthetic oligonucleotides designated in any of the tables herein.

The conditions for site specific mutagenesis can be generalized as follows. One ug of the single stranded DNA is hybridized with 5 ng of the phosphorylated mutagenic oligonucleotide(s) (23 mer to 25 mer encoding the appropriate mutation) and 1 ng of the M13 universal sequencing primer (17 mer purchased from P.L. Biochemicals) for 5 to 15 minutes at 55° C. in 0.01 ml solution of 10 mM Tris-HCl, pH 7.5, and 10 mM MgCl$_2$. The reaction is cooled to room temperature and then added to 0.01 ml of 0.12 mM dXTPs, 5 units Klenow fragment of DNA polymerase I (Boehringer Mannheim), 20 units of T4 DNA ligase (New England Biolabs), and incubated for 4–6 hours at 15° C. An aliquot (0.002 ml) of the reaction is then added to competent JM101 bacteria and plated overnight on L agar plates at 37° C. The DNA of the resulting M13 clones is transferred to each of two nitrocellulose filters, baked under vacuum at 80° C. for 2 hours and then incubated for 2 hours at 42° C. in pre-hybridization solution: 6×SSC (1×SSC is 150 mM NaCl, 15 mM sodium citrate, pH 7.0), 0.1% sodium dodecyl sulfate, 2×Denhardt's (0.05% ficoll, 0.05% polyvinylpyrrolidone, 0.05% bovine serum albumin) solution) and 0.4 mg/ml of denatured salmon sperm DNA. The filters are then incubated for 3 hours at 42° C. with fresh pre-hybridization solution containing the appropriate mutagenic oligonucleotide which has been 5'-end labeled with [lambda-$^{32}$P]-ATP and T4 polynucleotide kinase. The filters are then washed twice with 4×SSC at room temperature for 15 minutes, once for 15 minutes at 65° C., once at room temperature in TMACL solution (3M tetramethylammonium chloride, 50 mM Tris-HCl, pH 8.0, 2 mM EDTA, 0.1% SDS) and once at 65° C. in TMACL solution and then used to expose X-ray film overnight at room temperature. Clones corresponding to dark positives on the X-ray film are then picked from the original plate, the DNA is isolated and then analyzed for the mutated sequence by dideoxy sequencing. If two oligonucleotides are being used to produce a double mutant then one filter is screened with one oligonucleotide and the other filter is screened with the second oligonucleotide. Double mutants will have a positive signal with both oligonucleotides.

Figure 6:
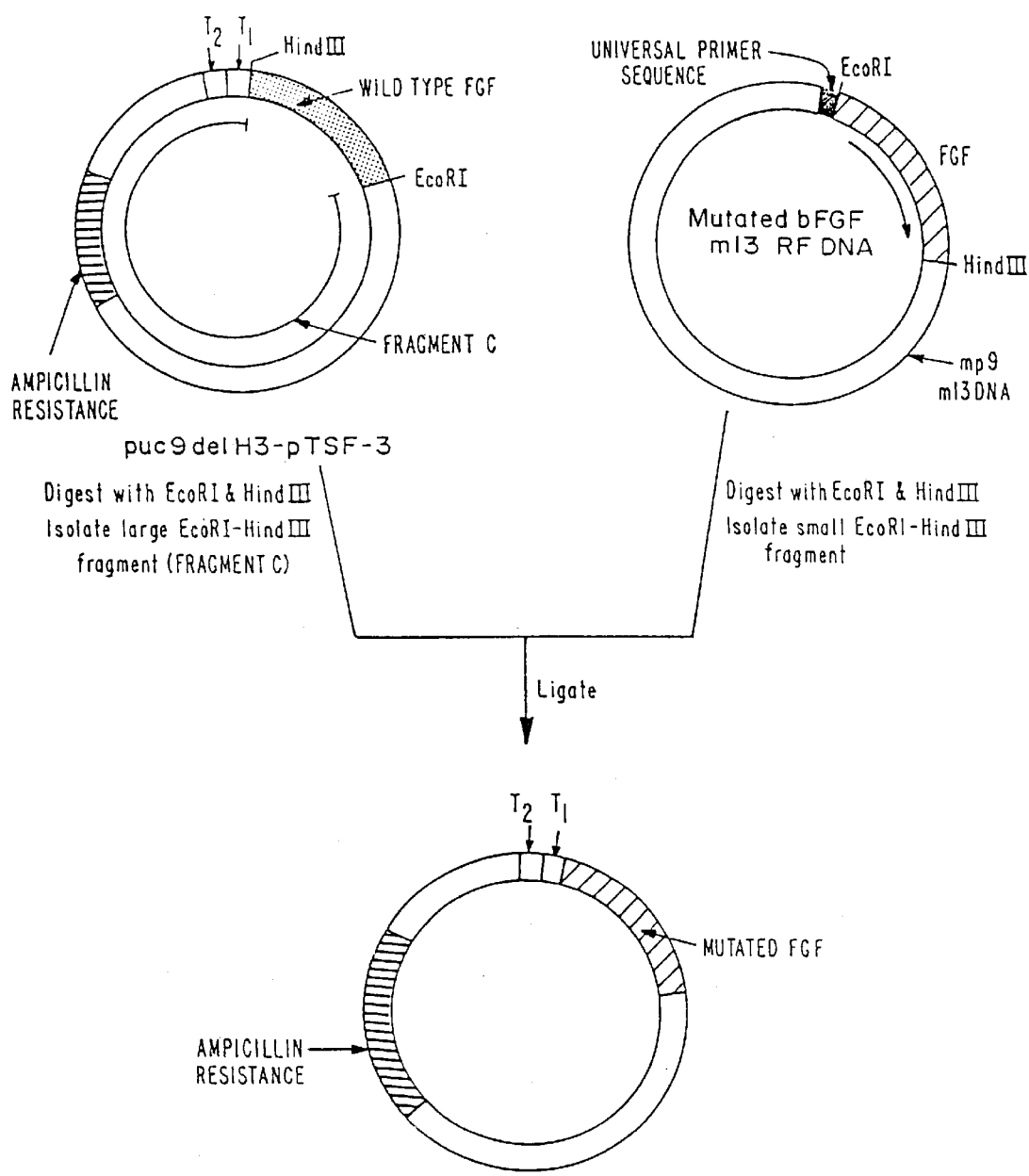
FIG. 6 is an illustration of the procedure used to insert any of the FGF analog gene sequences into the expression vector pUC9delH3-pTSF-3.

The DNA replicative form of the mutated M13 clone is then prepared, digested with EcoRI and HindIII, and the DNA fragment encoding the mutated FGF is isolated by agarose gel electrophoresis. The DNA fragment is then ligated to Fragment C of pUC9delH3-pTSF-3 (described in Example 3 and illustrated in FIG. 6), transfected into competent HB101 cells, and grown overnight on L agar plates supplemented with 100 ug/ml ampicillin. Colonies are selected, grown in L broth supplemented with 100 ug/ml ampicillin and then the plasmid DNA is isolated from the bacteria. The DNA is then used to transform competent E. coli B cells (Luria and Delbrck, Arch Biochem (1942) 1:111).

EXAMPLE 5

Preparation of Basic FGF Analog bFGF-C34/101S

In this example, cysteine residues at positions 34 and 101 of the human basic FGF protein were changed to serine residues thereby producing a double mutation. Approximately 2 micrograms each of the mutagenic 23-mer 5'-ACGTCTGTACTCCAAAAACGGTG-3' (SEQ ID NO: 22) (#2222); which alters the sequence at codon 34, and the mutagenic 23-mer 5'-TACAGACGAGTCTTTCTTTTTTG-3' (SEQ ID NO: 23) (#2323); which alters the sequence at codon 101 were incubated in 50 ul of 1×kinase/ligase buffer (7 mm Tris-HCl pH 7.6, 10 mm MgCl$_2$, 5 mm dithiothreitol) with 1 mM ATP and 5 units T$_4$ polynucleotide kinase for 30 minutes at 37° C. The phosphorylated oligonucleotides were diluted two-fold into 1 mM Tris-HCl, pH 8.0 and 1 mM EDTA.

One ug of the single stranded M13 template FGFt 7910 was incubated with 20 ng each of the phosphorylated oligonucleotides 2222 and 2323 and 1 ng of the universal M13 sequencing primer (New England Biolabs) in 10 ul of 10 mm Tris-HCl pH 7.5 and 10 mm MgCl$_2$ for 20 minutes at 55° C. and then at room temperature for 10 minutes. The reaction was then supplemented with 0.5 mM dXTPs, 5 units of the Klenow fragment of DNA polymerase I, 1 mM ATP, and 20 units T4 DNA ligase and incubated at 15 C. for 5 hours. 2 ul of the reaction was then used to transform competent JM101 bacteria. The transformed cells were plated overnight at 37° C., and the resulting M13 DNA was transferred to nitrocellulose filters as described above.

One ug of each of the oligonucleotides (#2222 and #2323) was phosphorylated as described above except 1 mCi of [lambda-$^{32}$P]-ATP (New England Nuclear #NEG035C, approximately 5 mCi/nmole) was substituted for cold ATP. The radioactive probes were then added separately to the duplicate filters and processed as described above. M13 clones corresponding to positive signals from the resulting autoradiographs were isolated and the single stranded M13 DNA prepared by the method of Sanger et al, supra. The resulting M13 DNA template (#8725) was analyzed by dideoxy sequencing and shown to contain the expected changes.

The double stranded replicative form (RF) of the M13 template #8725 was isolated by the method of Birnboim and Doly, *Nucl Acids Res* (1979) 7:1513–1519. In this procedure, fifty ul of M13 phage #8725, isolated from infected JM101, were used to inoculate 50 ml of a JM101 culture (saturated culture, 20×diluted into J broth) which were then grown for 6 hours at 37° C. The bacteria were harvested by centrifugation and the DNA isolated as described by Birnboim and Doly, supra. Approximately 5 ug of the RF DNA was cut in 0.4 ml of 1×HindIII buffer as described by the manufacturer with 40 units each of HindIII and EcoRI for 2 hours at 37° C. The reaction was then extracted twice with equal volumes of phenol/chloroform (1/1) and twice with chloroform and then ethanol precipitated. The resulting DNA was collected by centrifugation, washed with 70% ethanol, lyophilized, and resuspended in 20 ul of 1 mM Tris-HCl, pH 8.0, and 1 mM EDTA. The resulting EcoRI-HindIII fragment was isolated by agarose gel electrophoresis using GENECLEAN (BIO101 Inc.; La Jolla, Calif.) according to the manufacturer's instructions. Approximately 50 ng of the EcoRI-HindIII insert was ligated to the EcoRI-HindIII vector fragment C of pUC9delH3-pTSF-3 and used to transform competent MC1061 cells. The bacteria were processed as described in Example 7 in order to purify the analog and then the purified analog was tested for its ability to stimulate adrenal cortex endothelial (ACE) cells as described in Example 8.

Other mutants containing cysteine-to-serine substitutions have been constructed and expressed in bacteria. These constructions contain from one to four Cys →Ser substitutions. All of these substitutions result in the recovery of an FGF protein with varying levels of activity. The specific constructions are listed below in Table 1. Each of these FGF analog proteins has been isolated using a heparin affinity column.

TABLE 1

| bFGF Analog[†] | Oligonucleotide[#] | Number[*] |
|---|---|---|
| 1) bFGF-C78S | 5'-pCAAAGGAGTGTCTGCAAACCGTT (SEQ ID NO:24) | 2217 |
| 2) bFGF-C96S | 5'-pAGCTTCTAAATCTGTTACAGACG (SEQ ID NO:25) | 2218 |
| 3) bFGF-C78/96S | | 2218/2217 |
| 4) bFGF-C34/78/96/101S | | 2217/2218/2222/2323 |
| | 5'-pACGTCTGTACTCCAAAAACGGTG (SEQ ID NO:26) | 2222 |
| | 5'-pTACAGACGAGTCTTTCTTTTTTG (SEQ ID NO:27) | 2323 |
| 5) bFGF-C34/78/96S | | 2222/2218/2217 |
| 6) bFGF-C78/96/101S | | 2217/2218/2323 |
| 7) bFGF-C34/78/101S | | 2222/2217/2323 |
| 8) bFGF-C34/78S | | 2222/2217 |
| 9) bFGF-C34/101S | | 2222/2323 |

[†]Analogs of bFGF are designated as: bFGF-XYZ where X is the amino acid in the native human bFGF sequence that is being mutated, Y is the position of amino acid X, and Z is the amino acid residue that is being substituted for X at position Y. Multiple mutations are indicated. Mutations that involve the deletion of a region of the native bFGF protein are indicated with parenthesis (X-Z) with the deleted region defined by the amino acids included in residues X to Z.
[#]Oligonucleotide used for in vitro mutagenesis.
[*]Number of the oligonucleotide used for the mutagenesis.
NOTE: This legend is applicable to all of the following tables and analog descriptions. The one-letter code depicting specific amino acids is as follows:

| Amino Acid | Three-Letter abbreviation | One-Letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The bFGF analogs described below in Table 2 were tested for their ability to stimulate bovine adrenal cortex endothelial cell proliferation. As indicated below, the double mutant bFGF-C78/96S has enhanced activity compared to wild type bFGF. Any alteration of cysteines at the conserved positions 34 and 101, that is, positions conserved throughout the family of FGF-related molecules including human and bovine aFGF, bovine and xenopus bFGF, murine int-2, human hst and human KS3, significantly decreased the activity of the resulting analog.

TABLE 2

Activity of bFGF and Various Cysteine Analogs in the ACE Cell Proliferation Assay

| FGF ANALOG | % ACTIVITY |
|---|---|
| WILD TYPE bFGF | 100 |
| C78S* | 53 |
| C96S* | 95 |
| C78/96S* | 159 |
| C34/101S | 2 |
| C34/78/101S+ | 2 |
| C78/96/101S+ | 23 |
| C34/78/96/101S+ | 7 |

*Average of 2 independent assays.
+Average of 3 independent assays.

EXAMPLE 6

Heparin Binding Assay

The interaction of bFGF analogs with heparin is characterized by the ionic strength (NaCl concentration) of a Tris-HCl buffered solution required to elute the protein from heparin-Sepharose resin. This analysis determines the NaCl concentration required to remove the bFGF analogs that were bound to the heparin-Sepharose resin.

A heparin-5PW column was prepared by Bio-Rad Laboratories (Richmond, Calif.) by introducing heparin onto Bio-Gel TSK-50 resin. The column (75×7.5 mm I.D.; 4–6 mg/ml of heparin) was used with two Beckman model 110B Solvent Delivery Modules; a Beckman model #421 Controller, and a Kratos Spectraflow absorbance detector model #757. Samples were loaded onto the column in 0.5 M NaCl, 20 mM Tris HCl, pH 7.5 and then eluted with a gradient of 0.6–3.0 M. Protein was monitored by absorbance at 214 nm. The conductivity of various samples was tested and compared to buffered NaCl standards to determine NaCl concentrations along the gradient. Data from the absorbance detector was collected and analyzed using Access*Chrom (Nelson Analytical, Inc., Cupertino).

Figure 7:
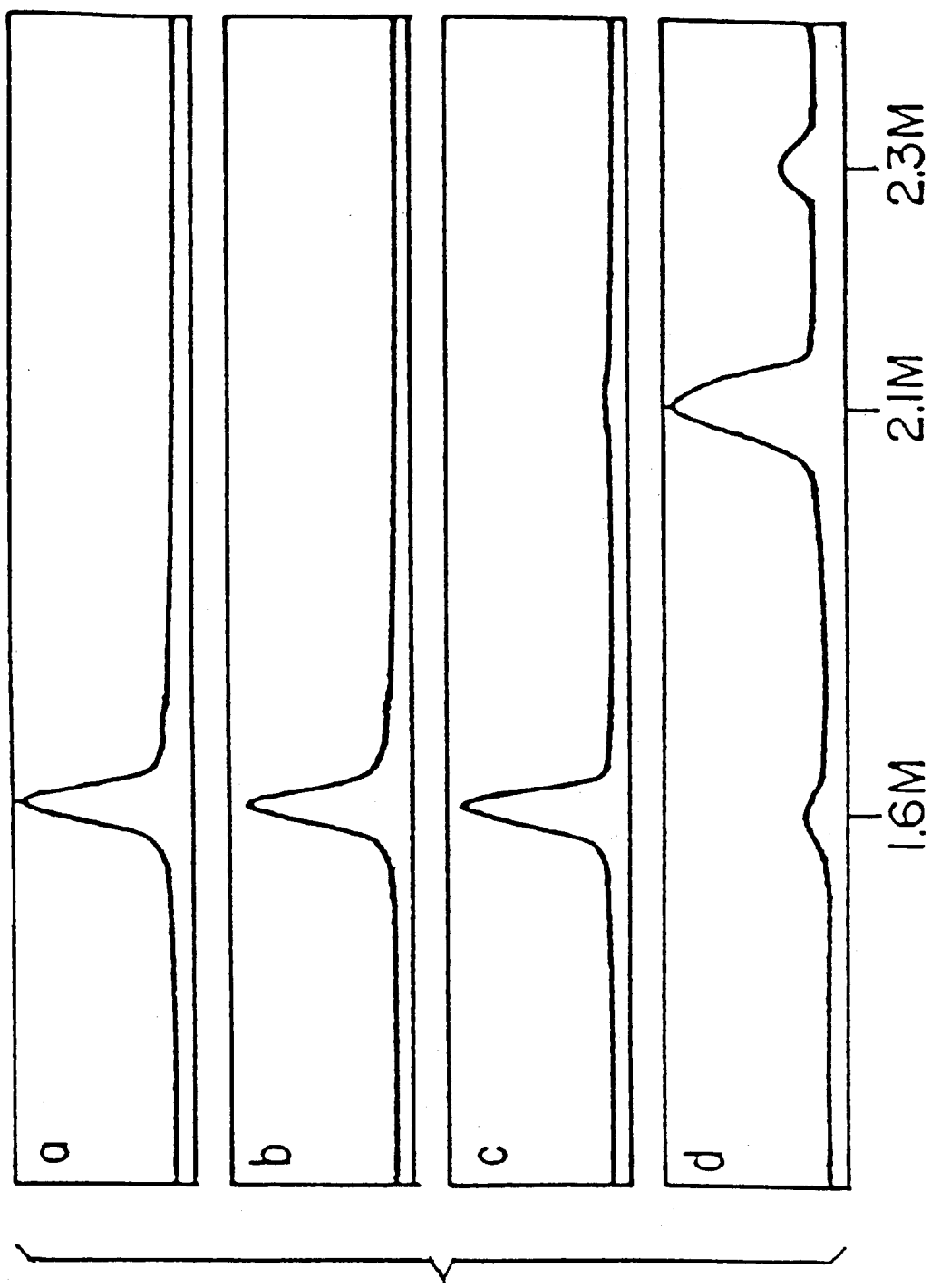
FIG. 7 shows the results of wild type bFGF as compared to the double cysteine substituted FGF analog, bFGF-C78/96S, using a high performance liquid chromatography (HPLC) heparin affinity column.

The cysteine-substituted FGF analogs of Example 5 were analyzed by heparin HPLC. The analog bFGF-C78/96S elutes as a single species with (FIG. 7a) and without (FIG. 7b) dithiothreitol treatment. This is in contrast to wild type bFGF which elutes as a single species with dithiothreitol treatment (FIG. 7c) but as a heterogeneous species in the absence of a reducing agent (FIG. 7d). In addition, the double mutant does not exhibit any heterogeneity when analyzed by reverse phase-HPLC or by size exclusion chromatography as is the case for wild type bFGF.

The single cysteine-substituted mutants, C78S and C96S, when analyzed as above, will also reduce the heterogeneity of the resulting product as compared to wild type bFGF.

The same supernatant fraction is tested for mitogenic activity using the endothelial cell proliferation assay or the Balb/c 3T3 thymidine uptake assay (Hauschka et al *J Biol Chem* (1986) 261:12665–12674) described below.

EXAMPLE 7

Isolation of Recombinant Human bFGF and Analogs of bFGF, and Characterization of the In Vitro Activity This will describe the procedure for isolating approximately 100 ug of recombinant bFGF from bacteria. The method can be scaled up to obtain larger quantities. Bacteria containing the appropriate plasmid are grown overnight in L broth supplemented with 100 ug/ml ampicillin. 0.2 ml of the culture are inoculated into 100 ml of 1×M9 salts (Maniatis et al, supra) 0.4% glucose, 2 ug/ml thiamine, 200 ug/ml $MgSO_4$.7 $H_2O$, 0.5% casamino acids, 100 uM $CaCl_2$ and 100 ug/ml ampicillin and grown on a shaker at 37° C. The culture is supplemented with 20 ug/ml indole acrylic acid upon reaching an optical density of 0.1 at a wavelength of 550 nm. The bacteria are harvested upon reaching an optical density of 1.0 by centrifugation (5000 rpm, 4° C., 15 minutes), quick frozen in a dry ice/ethanol bath and then stored at −80° C. The bacterial pellet is resuspended in 10 ml of 0.02 M Tris-HCl, pH 7.5, 0.6M NaCl, 1 mM PMSF, 80 ng/ml aprotinin, and 10 ug lysozyme and incubated at 4 C. for 15 minutes. The mixture is then sonicated 5 times at a setting of 3 using a Sonicator Cell Disruptor (Heat Systems). The reaction is then incubated with DNAseI (100 units) and RNAseA (100 units) for 15, minutes at 4° C. and then centrifuged for 15 minutes at 4° C. at 10,000 rpm. The supernatant is then loaded onto an 8.0 ml heparin-Sepharose column (Pharmacia) which has been prewashed with 3.0 M NaCl, 10 mM Tris-HCl, pH 7.5 and equilibrated with 0.6 M NaCl, and 0.02 M Tris-HCl pH 7.5. The column is washed with 0.6 M NaCl until no detectable protein, as judged by absorbance at 280 nm, is eluting off the column. The column is then washed with 1.0 M NaCl and the bound material eluted off with 2.0 M NaCl, 20 mM Tris-HCl, pH 7.5. This purification scheme can be performed in buffers in the presence or absence of 5 mM dithiothreitol.

EXAMPLE 8

Mitogenic Assays

FGF analogs are tested for either agonist or antagonist activity with respect to wild type FGF in an adrenal cortex capillary endothelial (ACE) cell proliferation assay as described by Gospodarowicz et al (*J Cell Physiol* (1985) 122:323–332). Individual analogs were tested as follows. Approximately 1×10 cells were plated in 2 ml of DME 16 supplemented with 10% calf serum, 50 units/well of penicillin and 50 units/well of streptomycin in a Falcon 6-well plate. Appropriate dilutions (1 pg/ml to 1 ug/ml final concentration) of each sample, as well as wild type (bovine pituitary basic) FGF were added in 10 ul volumes to the cells. As a negative control, 6 wells without added FGF samples were run simultaneously. The plates were incubated at 37° C. for 48 hours and cell samples were re-added to the appropriate well and incubated for an additional 48 hours at 37° C. Cells were then trypsinized, collected and counted in a Coulter counter.

Balb/c 3T3 cells, obtained from ATCC, were used to test for the ability of bFGF preparations to stimulate DNA synthesis essentially by the method described by Hauschka et al (1986) supra. Cells were seeded onto 96 well plates at a density of about 20,000/well in 0.2 ml Dulbecco's modified Eagle's medium (DME; GIBCO) containing 4.5 g/liter glucose, 2.2 g/liter $NaHCO_3$, 50 units/ml penicillin, 50 ug/ml streptomycin, and 10% calf serum (HYCLONE) and allowed to grow to confluency (2–3 days) in a 5% $CO_2$, 95% Air incubator at 37° C. Cultures were switched to serum free medium containing 0.01% bovine serum albumin, after which 0.01 ml of appropriate dilutions of test substance were added. Cultures were incubated at 37° C. for an additional 16 hr, after which the medium was changed to serum free medium containing 0.01% bovine serum albumin plus 50 uCi/ml of [³H] thymidine. Plates were then incubated for 2 hours after which TCA precipitable counts were determined as follows. The 96 well plate was placed on ice and the medium carefully removed, washed twice with cold PBS, followed by incubation with 10% trichloroacetic acid for 20 min at 4° C. Remaining radioactivity was solubilized in 0.1 N NaOH, and counted.

These assays were used to test the FGF analogs for their respective agonist or antagonist activity toward wild type basic FGF. The ability of FGF analogs to serve as antagonists to basic FGF is characterized by mixing appropriate quantities, such as 1–1000 ng, of the particular analog with 1 ng of basic FGF and testing the mixture in the above-described assays.

EXAMPLE 9

Construction of Receptor Binding FGF Analogs

A number of oligonucleotides were constructed and tested in an FGF receptor competitive binding assay. The specific mutants are provided below and include single amino acid substitutions, double amino acid substitutions and deletion mutations.

| Analog | Oligonucleotide | Number |
|---|---|---|
| bFGF-K35S | 5'-pGTCTGTACTGCTCAAACGGTGGTT (SEQ ID NO:28) | 2553 |
| bFGF-R42L | 5'-pTTTCTTCCTGCTCATCCACCCCG (SEQ ID NO:29) | 2327 |
| bFGF-D46A | 5'-pCATCCACCCCGCCGGCCGAGTGG (SEQ ID NO:30) | 2221 |
| bFGF-R48L | 5'-pCCCCGACGGCCTAGTGGACGGGG (SEQ ID NO:31) | 2454 |
| bFGF-R48A | 5'-pACCCCGACGGCGCAGTGGACGGGG (SEQ ID NO:32) | 2555 |
| bFGF-D50A | 5'-pCGGCCGGAGTGGCCGGGGTCCGCG (SEQ ID NO:33) | 2224 |
| bFGF-V52K | 5'-pGAGTGGACGGGAAACGCGAGAAGAG (SEQ ID NO:34) | 2491 |
| bFGF-R53L | 5'-pGGACGGGGTCCTCGAGAAGAGCG (SEQ ID NO:35) | 2220 |
| bFGF-K55M | 5'-pGGTCCGCGAGATGAGCGACCCAC (SEQ ID NO:36) | 2223 |
| bFGF-K55I | 5'-pGGTCCGCGAGATAAGCGACCCACA (SEQ ID NO:37) | 2567 |
| bFGF-D57A | 5'-pCGAGAAGAGCGCCCCACACATCA (SEQ ID NO:38) | 2225 |
| bFGF-H59N | 5'-pGAGCGACCCAAACATCAAACTAC (SEQ ID NO:39) | 2383 |
| bFGF-R90T | 5'-pAGAAGATGGAACTTTACTAGCTTC (SEQ ID NO:40) | 3088 |
| bFGF-D99A | 5'-pATGTGTTACAGCAGAGTGTTTCT (SEQ ID NO:41) | 2381 |
| bFGF-E100A | 5'-pGTTACAGACGCCTGTTTCTTTTTG (SEQ ID NO:42) | 2549 |
| bFGF-E100S | 5'-pGTGTTACAGACAGTTGTTTCTTTTT (SEQ ID NO:43) | 2380 |
| bFGF-E105S | 5'-pGTTTCTTTTTTTCACGATTGGAGT (SEQ ID NO:44) | 2556 |
| bFGF-R106L | 5'-pCTTTTTTGAACTATTGGAGTCTA (SEQ ID NO:45) | 2494 |
| bFGF-E108A | 5'-pTGAACGATTGGCATCTAATAACTA (SEQ ID NO:46) | 2554 |
| bFGF-Y112A | 5'-pAGTCTAATAACGCAAATACTTACCG (SEQ ID NO:47) | 2450 |
| bFGF-N113S | 5'-pCTAATAACTACAGTACTTACCGG (SEQ ID NO:48) | 2452 |
| bFGF-R116T | 5'-pCAATACTTACACTTCAAGGAAATA (SEQ ID NO:49) | 3091 |
| bFGF-R118L | 5'-pCAATACTTACCTGTCAAGGAAAT (SEQ ID NO:50) | 2483 |
| bFGF-K119S | 5'-pACCGGTCAAGGTCTTACACCAGTTG (SEQ ID NO:51) | 2548 |
| bFGF-(41-43) | 5'-pGGTGGTTTCTTCCACCCCGACGGC (SEQ ID NO:52) | 2336 |
| bFGF-(49-51) | 5'-pCCCGACGGCCGAGTCCGCGAGAAG (SEQ ID NO:53) | 2335 |
| bFGF-(62-64) | 5'-pCCACACATCAAACAAGCAGAAGAG (SEQ ID NO:54) | 2334 |
| bFGF-(83-85) | 5'-pGCAAACCGTTACAAAGAAGATGGA (SEQ ID NO:55) | 2333 |
| bFGF-(105-107) | 5'-pTGTTTCTTTTTTGAGTCTAATAAC (SEQ ID NO:56) | 2332 |
| bFGF-(112-114) | 5'-pGAGTCTAATAACTACCGGTCAAGG (SEQ ID NO:57) | 2337 |

The FGF analogs were produced as described in Example 7 using an appropriate expression vector, such as plasmid pUC9delH3-pTSF11-3 or pUC9-pTSF11, and isolated by heparin-Sepharose chromatography.

A competitive binding assay was established to determine the relative affinity of FGF analogs compared to that of recombinant basic FGF for the FGF receptor. Analogs having high affinity for the FGF receptor and reduced mitogenic activity are designated potential FGF antagonists.

The assay involved binding saturating concentrations of [$^{125}$I]-basic recombinant FGF (10 ng/ml) to Balb/c 3T3 cells in the presence of various concentrations of unlabeled FGF or analogs. The binding was conducted at 4° C. for 3–4 hours to establish equilibrium. The cells were then washed 12× with a 0.1% gelatin, 2 N NaCl balanced salt solution containing 50 mM Hepes to maintain the pH at 7.5. Cells were solubilized in 1 N NaOH and cell-associated radioactivity measured. Following this procedure, the non-specific binding was kept at or below 5%. The affinity of an analog for the FGF receptor was determined relative to that of bovine pituitary FGF by taking the ratio of the concentration of analog that inhibits specific binding by 50% over the concentration of FGF that inhibits specific binding by 50%. A ratio of less than 1 indicated that the analog has a higher affinity for the FGF receptor than FGF and a ratio of greater than 1 indicated that the analog has a lower affinity for the FGF receptor than FGF.

A number of analogs that had reduced mitogenic activity in the ACE assay had equal or higher affinity for the FGF receptor compared to bovine pituitary FGF. Those mutants that had less than 5% of wild type activity in the ACE assay but had equal or higher affinity for the FGF receptor include: R31S, K35S, D46A, R48L, D50A, V52K, R53L, R90T, E100S, E100A, R106L, R116T, R118L, K119S. These compounds may be useful as antagonists.

These analogs were also tested for mitogenic ability using either one of the previously described assays. The results are provided below in Table 3.

TABLE 3

Activities of FGF Analogs

| Analog | 3T3 Mito. Heparin −/+ | ACE Mito. Heparin −/+ | FGF-Rc Comp. Heparin −/+ | Heparin Elution |
|---|---|---|---|---|
| hFGF(b) (EC$_{50}$) | 100%/100% (630 pg/ml) | 100%/100% (160 pg/ml) | 1.0/1.0 (10 ng/ml) | 1.58 M |
| hFGF(b) 25–155 | 50%/100% | | | 1.62 M |
| hFGF(a) | 5%/25% | 0.01%/10% | 0.5/ | 1.23 M |
| bba* | <0.2%/100% | | 0.3/ | 1.43 M |
| K27M | | | 0.3/0.2 | |
| D28K | | 8.8%/ | 1.0/1.3 | |
| KKR# | 8.5%/8.5% | 0.11%/4.2% | | ~1.5 M |
| R31S | 100%/100% | 0.45%/17.8% | 1.0/0.8 | |
| K35S | | 2.6%/55.5% | 0.1/0.05 | 1.23 M |
| D46A | | 2.8%/ | 0.5/ | |
| R48L | | 1.7%/ | 0.16/2.0 | |
| R48A | | 8.9%/84.2% | 0.32/0.3 | |
| D50A | | 0.37%/ | 2.5/2.5 | |
| V52K | | 0.72%/>20% | 0.5/0.4 | |
| R53L | | 0.5%/ | 0.22/0.25 | 1.56 M |
| K55I | 1%/8% | <0.1%/4.2% | 2.0/1.6 | |
| K55M | | 90%/ | 0.4/0.4 | |
| D57A | | 0.27% | | |
| H59N | 315%/ | 42%/120% | 0.4/0.4 0.13/0.08 | |
| R90T | 77%/216% | 2.68%/95.4% | 0.6/0.5 | 1.58 M |
| hFGF(b) (EC$_{50}$) | 100%/100% (630 pg/ml) | 100%/100% (160 pg/ml) | 1.0/1.0 (10 ng/ml) | 1.58 M |

TABLE 3-continued

Activities of FGF Analogs

| Analog | 3T3 Mito. Heparin −/+ | ACE Mito. Heparin −/+ | FGF-Rc Comp. Heparin −/+ | Heparin Elution |
|---|---|---|---|---|
| K95T | 100%/170% | 44.9%/ | | 1.58 M |
| D99A | 150%/280% | 19.2%/ | 0.04/0.03 | 1.53 M |
| E100S | | 0.03%/ | 1.1/0.5 | |
| E100A | | 0.75%/ | 0.8/1.0 | |
| E105S | 12.6%/100% | 0.3 | 50/40 | |
| R106L | 20%/200% | 0.27%/ | 0.3/0.13 | 1.55 M |
| R106T | 210%/250% | 9.1%/62.5% | | 1.58 M |
| E108A | 180%/ | 30%/ | 2.5/2.5 | |
| Y112A | 0.2%/0.2% | 0.01%/4.3% | 100/100 | 1.49 M |
| N113S | 160%/ | 7.7%/ | 1.0/1.0 | |
| R116T | 50%/300% | 0.64%/ | 0.2/ | 1.53 M |
| R118L | | 1.8%/ | 0.5/0.4 | |
| K119S | 48%/250% | 0.6%/41% | 0.35/0.25 | 1.58 M |
| K128S | 210%/ | 68%/ | 0.3/0.25 | 1.38 M |
| K128E | 200%/140% | 13%/ | | 1.04 M |
| R129T | 87%/190% | 11.9%/ | 1.3/0.5 | 1.45 M |
| R129L | | 1.3%/ | | |
| KR128, 129ST | 185%/ | 8.4%/ | 2.0/0.8 | 1.14 M |
| K134S | | | | 0.6 M |
| K138S | | | | 1.0 M |
| C78S | | 53%/123% | 0.3/0.25 | 1.57 M |
| C96S | | 95%/96% | 0.3/0.8 | 1.58 M |
| C78,96S | 118%/160% | 159%/151% | 0.2/0.1 | 1.58 M |
| C34,101S | | 2%/ | | |
| C34,78,101S | 65%/144% | 2%/72% | 0.45/0.5 | 1.50 M |
| C78,96,101S | | 23%/125% | | |
| C34,78,96, 101S | | 7%/119% | 1.0/0.5 | 1.51 M |

*bba is hFGF(b) with hFGF(a) substitutions for aa 95–155.
KKR has neutral substitutions (M, S or T) for K27, K30 & R31.
@C-4-S has 4 S substitutions for each of the 4 Cs.

Legend:
The data indicate the activities of the various FGF analogs relative to the activity of wild type FGF. The first row indicates the actual ED$_{50}$ value for wild type FGF in each assay (in parentheses). The ED$_{50}$ is the concentration at which the analog elicits a half-maximal response in the assay and is therefore a measure of potency. For analogs exhibiting activity lower than wild type activity, higher concentrations are required to elicit activity equivalent to wild type FGF. Therefore, the ED$_{50}$ values of such analogs are higher than wild type (more analog required to elicit half-maximal stimulation).

For analogs exhibiting activity higher than wild type activity, less analog is required to elicit activity equivalent to wild type activity. Therefore, the ED$_{50}$ values of such analogs are lower than wild type (less analog required to elicit half-maximal stimulation). The ED$_{50}$ values for the various analogs in each assay are indicated as a percentage of wild type activity (the ED$_{50}$ of wild type FGF divided by the ED$_{50}$ of the analog times 100%). Therefore, analogs exhibiting values greater than 100% appear to have activity greater than wild type FGF in the assay, while analogs exhibiting values less than 100% appear to have activity less than wild type FGF in the assay.

"3T3 Mito./Heparin −/+":
The data reflect the activity observed in the 3T3/Balb/c cell mitogenic assay (thymidine uptake) relative to the activity observed for wild type FGF in this assay. Activity values obtained in the absence or presence of 1 ug/ml heparin are indicated to the left and right of the slash respectively.

"ACE Mito./Heparin −/+":
The data reflect the activity observed in the Adrenal Cortical Endothelial cell proliferation assay relative to the activity observed for wild type FGF in this assay. Activity values obtained in the absence or presence of 1 ug/ml heparin are indicated to the left and right of the slash respectively.
"FGF-Rc Comp./Heparin −/+":
The data reflect the relative ability of the analog to bind the FGF receptor as measured in the competitive binding assay. The values are the ratio of the $ED_{50}$ of the analog to the $ED_{50}$ of wild type FGF in this assay. Therefore, analogs which exhibit values less than 1.0 appear to have an affinity for the receptor which is greater than that of wild type FGF. Analogs which exhibit values greater than 1.0 appear to have an affinity for the receptor which is less than that of wild type FGF. Activity values obtained in the absence or presence of 1 ug/ml heparin are indicated to the left and right of the slash respectively.
Analogs which exhibit near wild type receptor activity and exhibit low relative activity in the mitogenic assays are potential antagonists.
"Heparin/Elution":
The data indicate the approximate salt (NaCl) concentration at which the analog elutes from an heparin-TSK column during high performance liquid chromatography. Analogs exhibiting values less than 1.58 M appear to have reduced heparin binding as judged by this procedure. Analogs exhibiting values app. equal to 1.58 (1.53 to 1.63) appear to have affinity for heparin which is insignificantly changed from that of wild type bFGF as judged by this procedure.

EXAMPLE 10

Reduced Heparin Binding FGF Analogs

FGF analogs were constructed wherein mutagenesis was targeted for the region of the basic FGF molecule which may be involved in binding heparin and heparin-like compounds. The analogs, with the specific oligonucleotide sequences which correspond to the amino acid to be changed, are listed below.

encompassing residues 128–138 is a targeted heparin binding region as amino acid substitutions in this region has led to a decrease in heparin binding as measured by elution from the heparin-SPW resin.

EXAMPLE 11

Preparation of an FGF Antagonist by N-terminal Deletion

The blunted NdeI-HindIII FGF fragment from pUC9delH3-PTSF-3 was subcloned into the SmaI-HindIII site of M13mp18. An oligo was used to introduce a new NdeI site in the FGF molecule at amino acid 25 using in vitro mutagenesis. The new NdeI site serves as both a new restriction site for subcloning the FGF fragment and also as a new translational start site for the shortened form of FGF. The mutagenic oligo used has the sequence:

5'-TTG GGT CTT TGA AGT GCA TAT GTG GGA AGG CAC CAG (SEQ ID NO: 69)

The shortened FGF was subcloned into pTSF-delbeta-gal for expression as an NdeI-HindIII fragment and the resulting plasmid designated bFGF(25–155). Protein sequence confirmed that the N-terminus of the protein is histidine. pTSF-delbeta-gal was constructed by digesting pTSF11 with PvuII and EcoRI, thereby deleting approximately one-half of the beta-gal promoter operator.

The N-terminal deletion analog, bFGF(25–155) was purified by heparin-Sepharose chromatography as above. This analog exhibits agonist activity in the 3T3 mitogenic assay with an $ED_{50}$ similar to that of bFGF. Although stimulation in the 3T3 assay peaks at approximately 1 ng/ml for both wild type and bFGF(25–155) the level of stimulation for the analog (determined in the absence of heparin) is not as great as observed for wild type bFGF. Thus, bFGF(25–155) displays characteristics of a partial agonist. In addition,

| Analog | Oligonucleotide | Number |
|---|---|---|
| bFGF-K27M | 5'-pAGGTCACTTCATGGACCCAAAACG (SEQ ID NO:58) | 2487 |
| bFGF-K30A | 5'-pTCAAAGACCCAGCACGTCTGTACT (SEQ ID NO:59) | 2566 |
| bFGF-R31S | 5'-pAAGACCCAAAATCTCTGTACTGCA (SEQ ID NO:60) | 2568 |
| bFGF-D28K | 5'-pGTCACTTCAAAAAGCCAAAACGTCT (SEQ ID NO:61) | 2480 |
| bFGF-R118L | 5'-pCAATACTTACCTGTCAAGGAAAT (SEQ ID NO:62) | 2483 |
| bFGF-K35S | 5'-pGTCTGTACTGCTCAAACGGTGGTT (SEQ ID NO:63) | 2553 |
| bFGF-K128S | 5'-pATGTGGCACTGGAGCGAACTGGGCA (SEQ ID NO:64) | 2545 |
| bFGF-K128E | 5'-pATGTGGCACTGGAGCGAACTGGCCA (SEQ ID NO:65) | 3332 |
| bFGF-R129T | 5'-pGGCACTGAAAACTACTGGGCAGT (SEQ ID NO:66) | 3087 |
| bFGF-k128E/R129T | | |
| bFGF-K134S | 5'-pCTGGGCAGTATTCTCTTGGATCCAA (SEQ ID NO:67) | 3212 |
| | | 3212 |
| bFGF-K138S | 5'-pAACTTGGATCCTCTACAGGACCTGG (SEQ ID NO:68) | 3215 |

These gene sequences were inserted into an appropriate expression vector as taught previously and the resulting protein tested for reduced heparin binding activity. The results provided in Table 3 indicate that the region of bFGF concentrations of the bFGF(25–155) analog greater than 1 ng/ml result in apparent inhibition of activity; whereas for wild type bFGF, activity in the 3T3 assay peaks at approximately 1 ng/ml and is not significantly reduced even at 1 ug/ml, the activity of bFGF(25–155) at 10 ng/ml is approximately 15% that for wild type bFGF and at 100 ng/ml, bFGF(25–155) essentially lacks activity.

The FGF analog bFGF(25–155) is an FGF antagonist as determined by its ability, at concentrations of 1 ng/ml or greater, to inhibit the activity of wild type FGF in the absence of heparin. The activity elicited by 1 ng/ml wild type bFGF is reduced approximately 50% in the presence of 1 ng/ml bFGF(25–155), reduced approximately 75% in the presence of 10 ng/ml bFGF(25–155), and reduced by more than 95% in the presence of 100 ng/ml bFGF(25–155). That this inhibition is competitive is demonstrated by the shift in the $ED_{50}$ for wild type bFGF observed in the presence of bFGF(25–155). The ED for wild type bFGF is less than 1 ng/ml in the absence of the analog bFGF(25–155), approximately 10 ng/ml in the presence of 10 ng/ml bFGF(25–155), and approximately 100 ng/ml in the presence of 100 ng/ml bFGF(25–155). These data suggest that bFGF(25–155) binds the FGF receptor, probably with an affinity similar to that of wild type FGF, but bFGF(25–155) exhibits altered (reduced) activity. Thus, in the absence of heparin, the FGF analog bFGF(25–155) is a competitive inhibitor of wild type FGF and is therefore an antagonist.

While the FGF analog bFGF(25–155) has demonstrated FGF antagonist activity, it retains partial agonist activity. In addition, the agonist activity of this analog is enhanced, and the antagonist activity inhibited, by the presence of heparin. Therefore it is desirable to make additional alterations in the sequence to further reduce the activity of the analog without significantly reducing its affinity for the FGF receptor. The reason for the reduced activity of bFGF(25–155) is not known, however, it is presumed that the integrity of the N-terminal segment of wild type FGF is necessary for full activity. Therefore it is possible that further deletions and/or amino acid substitutions in the N-terminal region exclusive of the receptor binding domain will further diminish activity without reducing receptor binding. For example, deletions in the region of amino acids 25 to 33 may accomplish this end. Another approach would be to delete or alter amino acids in other, non-receptor binding domains such as amino acids 78–98 or 130–155. Finally, since the antagonist activity of this analog is inhibited by heparin, introducing substitutions which reduce heparin binding may reduce agonist activity and increase relative antagonist activity. These approaches may be used in combination and are considered within the scope of the present invention.

EXAMPLE 12

Construction of Expression Vectors and Stable Expression of FGF Analogs in Mammalian Cells The DNA sequences encoding FGF are most conveniently used to produce the recombinant proteins in a variety of hosts, as set forth in ||C.1 above. However, expression in mammalian systems is an alternative to bacterial expression as the mammalian host is capable of post translational processing analogous to that experienced by the natively produced protein.

To construct the vectors, the cloned FGF-encoding analog is excised with EcoRI and HindIII, provided with EcoRI or other appropriate linkers if necessary, and then inserted into an appropriate host vector such as pHS1 or its derivatives as described below.

Construction of Host Vectors pHS1

The plasmid pHS1 is suitable for expression of inserted DNA in mammalian hosts. It contains 840 bp of the hMT-II sequence from p84H (Karin, M., et al, *Nature* (1982) 299: 297–802) which spans from the HindIII site at position −765 of the hMT-II gene to the BamHI cleavage site at base +70. To construct pHS1, plasmid p84H was digested to completion with BamHI, treated with exonuclease BAL-31 to remove terminal nucleotides, and then digested with HindIII. The desired 840 bp fragment was ligated into pUC8 (Vieira, J., et al, *Gene* (1982) 19: 259–268) which had been opened with HindIII and HincII digestion. The ligation mixture was used to transform *E. coli* HB101 to $Amp^R$, and one candidate plasmid, designated pHS1, was isolated and sequenced by dideoxy sequencing. pHS1 contains the hMT-II control sequences upstream of a polylinker containing convenient restriction sites.

The workable host plasmid pHS1 can be further modified to contain additional control elements besides the metallothionein promoter. In particular, the enhancer elements of viral systems, such as SV40, can be included, as well as termination signals associated with the 3' untranslated regions of other proteins such as hGH.

Viral Enhancer

A pair of host expression vectors containing the SV40 enhancer in operable linkage to the MT-II promoter was constructed by inserting an 1120 bp SV40 DNA fragment into the HindIII site preceding the MT-II promoter sequences in pHS1. The SV40 DNA fragment spans the SV40 origin of replication and includes nucleotide 5171 through nucleotide 5243 (at the origin), the duplicated 72 bp repeat from nucleotide 107–250, and continues through nucleotide 1046 on the side of the origin containing the 5' end of late viral mRNAs. This HindIII 1120 bp fragment is obtained from a HindIII digest of SV40 DNA (Buchman, A. R., et al, *DNA Tumor Viruses,* 2d ed (J. Tooze, ed.), Cold Spring Harbor Laboratory, New York (1981), pp. 799– 841), and cloned into pBR322 for amplification. The cloning vector was cut with HindIII, and the 1120 bp SV40 DNA fragment isolated by gel electrophoresis and ligated into HindIII-digested, CIP-treated, pHS1. The resulting vectors, designated pHS1-SV(9) and pHS1-SV(10), contain the fragment in opposite orientations preceding the MT-II promoter. In pHS1-SV(9), the enhancer is about 1600 bp from the 5' mRNA start site; in the opposite orientation it is approximately 980 bp from the 5' mRNA start site. Both orientations are operable, but the orientation wherein the enhancer sequences are proximal to the start site provides higher levels of expression. It is believed that deletions which place the enhancer 250–400 bp upstream of the transcription start are optimal.

Additional vectors were constructed which place the SV40 enhancer 3' terminus 190 bp, 250 bp, and 360 bp respectively upstream from the 5' end of the MT promoter TATA box. The constructions were based on the mapping of the upstream regulatory regions of the human MT promoter described by Karin, M., et al, *Nature* (1984) 308:513–519. All constructions retain the sequences containing the duplicated sites for regulation by heavy metals, but the constructions with the 190 bp and 250 bp separations do not retain the sequence for glucocorticoid regulation which is further upstream from these sites.

These vectors, designated pHS'-SV190, pHS'-SV250, and pHS'-SV360 are prepared as follows; all constructions are identical except for the length of sequence containing the metallothionein promoter and upstream region which is supplied as a fragment excised from pHS1.

For pHS'-SV190, pHS1 is digested with SacII, blunted, and ligated to KpnI linkers. The DNA is then digested with EcoRI and KpnI to liberate the appropriate portion of the MT-II control sequences. Similarly, for pHS'-SV250, pHS1 is digested with HgaI, blunted, ligated to KpnI linkers and digested with EcoRI and KpnI; for pHS'-SV360, DdeI is used in the initial digestion.

An intermediate vector containing the SV40 enhancer is prepared by inserting the HindIII/KpnI fragment of SV40 (which extends from position 5171 to position 294 and which contains the enhancer element 50 bp from the KpnI site) into KpnI/HindIII digested pUC19 to obtain pUC-SV. (pUC19 contains three convenient restriction sites in the polylinker region, in order, HindIII, KpnI, and EcoRI.) The finished vectors are obtained by inserting the KpnI/EcoRI fragments prepared as described above into KpnI/EcoRI digested pUC-SV.

All of the foregoing modified vectors, thus, take advantage of the SV40 enhancer element. Other viral enhancers could, of course, be used in an analogous manner.

Transcription Termination Sequences

To provide transcription termination control sequences, DNA representing the coding sequence and 3' untranslated sequence of human growth hormone was ligated into pHS1. The intermediate vector can provide the hGH 3' untranslated sequence to coding sequences subsequently ligated into the vector in place of the hGH coding sequence.

The genomic sequences encoding hGH were isolated from p2.6–3 (DeNoto, et al, *Nucleic Acids Res* (1981) 19:3719) by digestion with BamHI, which cuts at the 5' end of the first exon, and EcoRI, which cuts 3' of the functional gene, followed by polyacrylamide gel purification. The isolated fragment was ligated into BamHI/EcoRI digested pHS1 and the ligation mixture transformed into *E. coli* MC1061 to Amp$^R$. Successful transformants were screened by restriction analysis, and a strain containing the desired plasmid, pMT-hGHg, was further propagated to prepare quantities of plasmid DNA.

In a manner similar to that described above for constructing pHS1-SV(9) or pHS1-SV(10), but substituting for pHS1, pMT-hGHg, a pair of vectors containing the hGH gene under the control of the MT promoter, and operably linked to SV40 enhancer, and designated, respectively, phGHg-SV(9) and phGHg-SV(10), were obtained. The ligation mixtures were used to transform *E. coli* 1061 to Amp$^R$, and the correct constructions verified.

Construction of Expression Vectors phGHg-SV(10) is then used as a host vector to accommodate the DNA sequences encoding any of the FGF analogs. phGHg-SV(10) is digested with BamHI and SmaI, blunted with Klenow, and treated with CIP to excise the hGH coding sequence. This opened vector is ligated to an NdeI(blunt)/HindIII(blunt) FGF analog fragment to obtain the desired expression vector pFGF-SV(10).

In addition, other host vectors may be used to obtain expression of these sequences, including pHS1 and pHS1 modified to contain the various configurations of SV enhancer as above described. Insertion is by analogous means, using BamHI/EcoRI digestion of the host vector. Also, DNA modified to encode any of the "long", "primary" or "short" forms of the acidic or basic FGF analogs may be employed.

These vectors are generically designated PMT-FGF for the purposes of the discussion below.

Production of FGF by Mammalian Recombinants

Chinese hamster ovary (CHO)-K1 cells are grown on medium composed of a 1:1 mixture of F12 medium and DME medium with 12% fetal calf serum. The competent cells are co-transformed with pMT-FGF and pSV2:NEO (Southern, P., et al, *J Mol Appl Genet* (1982) 1: 327–341). pSV2:NEO contains a functional gene conferring resistance to the neomycin analog G418. In the transformation, 500 ng of pSV2-NEO and 5 ug of pMT-FGF are applied to a 16 mm dish of cells in a calcium phosphate-DNA co-precipitate according to the protocol of Wigler, M., et al, *Cell* (1979) 16: 777–785, with the inclusion of a two minute "shock" with 15% glycerol after four hours of exposure to the DNA. A day later, the cells are subjected to 1 mg/ml G418 to provide a pool of G418-resistant colonies, which are assayed for FGF production and then can be cloned out.

Successful transformants, also having a stable inheritance of pMT-FGF, are plated at low density for purification of clonal isolates. Small amounts of these isolates are grown in multi-well plates after exposure to $10^{-4}$ M zinc chloride for convenient assay of FGF production. FGF determinations are made by standard ELISA or radio-immunoassays against the antisera prepared against the appropriate FGF protein analog using standard methods. Clonal isolates which produce large amounts of the desired FGF analogs are selected.

The cells, which have been shown to produce FGF analogs under suitable conditions, are seeded at 1/10 confluency in basal medium supplemented with 10% fetal calf serum, incubated overnight, and then induced for FGF production by addition of zinc chloride in the concentration range of $1\times10^{-4}$ M to $3\times10^{-4}$ M. FGF levels rise for 7–10 days, under optimal inducing conditions, $2\times10^{-4}$ M $ZnCl_2$.

If desired, the FGF analog can be obtained from the lysed cells and purified according to the procedures set forth above for the native protein, or by other standard methods known in the art.

In addition, as discussed above, secretion of the FGF protein analogs produced by the foregoing constructs can be achieved by exocytosis initiated by a calcium ionophore or other suitable stimulant. While it is not expected that proteins produced by CHO cells, specifically, would be released by LPS or phorbol ester stimulation, for example, by substituting for CHO cells, cell lines derived from macrophage as recombinant hosts, such secretion can be effected. Also, by altering the construction so as to provide a signal sequence secretion using the normal constitutive pathways could also be effected using CHO or other mammalian cell hosts. Effecting secretion has some advantages, of course, since the protein purification task becomes much simpler.

On or before Sep. 9, 1985, Applicants deposited with the American Type Culture Collection (ATCC), Rockville, Md., USA, the lambda phage lamdaBB2 which was assigned ATCC accession number 40196. On or before Sep.12, 1986, conditions of deposit for lambdaBB2 (ATCC 40196) was converted to conform to those specified under the Budapest Treaty on the International Recognition of the Deposit of Microorganisms (Budapest Treaty). Availability of the deposited strain is not to be construed as a license to practice the invention in contravention of the rights granted under the authority of any government in accordance with its patent laws.

What is claimed is:

1. An isolated DNA molecule encoding a human basic fibroblast growth factor wherein the cysteine residues at positions 78 and 96 are replaced by serine residues.

2. A recombinant vector comprising the DNA molecule of claim 1.

3. A host cell comprising the recombinant vector of claim 2.

4. A host cell of claim 3 wherein the cell is a eukaryotic cell.

5. A host cell of claim 3 wherein the cell is a prokaryotic cell.

6. A method of producing a basic fibroblast growth factor polypeptide in which the cysteine residues at positions 78 and 96 are replaced by serine residues, comprising the steps of culturing the host cells of claim 3 and isolating said polypeptide.

* * * * *